(12) United States Patent
Cipoletti et al.

(10) Patent No.: US 8,267,939 B2
(45) Date of Patent: Sep. 18, 2012

(54) TOOL FOR IMPLANTING EXPANDABLE INTERVERTEBRAL IMPLANT

(75) Inventors: Robert Cipoletti, Pompton Plains, NJ (US); Thomas Alheidt, Stockholm, NJ (US)

(73) Assignee: Stryker Spine (FR)

( * ) Notice: Subject to any disclaimer, the term of this patent is extended or adjusted under 35 U.S.C. 154(b) by 995 days.

(21) Appl. No.: 12/072,912

(22) Filed: Feb. 28, 2008

(65) Prior Publication Data

US 2009/0222100 A1 Sep. 3, 2009

(51) Int. Cl.
*A61B 17/60* (2006.01)
*A61F 2/44* (2006.01)

(52) U.S. Cl. .......................................... 606/99
(58) Field of Classification Search .................... 606/90, 606/99, 246, 259, 282
See application file for complete search history.

(56) References Cited

U.S. PATENT DOCUMENTS

| | | |
|---|---|---|
| 3,426,364 A | 2/1969 | Lumb |
| 3,486,505 A | 12/1969 | Morrison |
| 4,309,777 A | 1/1982 | Patil |
| 4,401,112 A | 8/1983 | Rezaian |
| 4,522,200 A | 6/1985 | Stednitz |
| 4,545,374 A | 10/1985 | Jacobson |
| 4,553,273 A | 11/1985 | Wu |
| 4,599,086 A | 7/1986 | Doty |
| 4,636,217 A | 1/1987 | Ogilvie et al. |
| 4,657,550 A | 4/1987 | Daher |
| 4,733,665 A | 3/1988 | Palmaz |
| 4,863,476 A | 9/1989 | Shepperd |
| 4,936,851 A | 6/1990 | Fox et al. |
| 5,059,193 A | 10/1991 | Kuslich |
| 5,171,278 A | 12/1992 | Pisharodi |
| 5,192,327 A | 3/1993 | Brantigan |
| 5,390,683 A | 2/1995 | Pisharodi |
| 5,425,772 A | 6/1995 | Brantigan |
| 5,484,437 A | 1/1996 | Michelson |
| 5,522,899 A | 6/1996 | Michelson |
| 5,554,191 A | 9/1996 | Lahille et al. |
| 5,562,736 A | 10/1996 | Ray et al. |
| 5,571,190 A | 11/1996 | Ulrich et al. |
| 5,571,192 A | 11/1996 | Schonhoffer |
| 5,593,409 A | 1/1997 | Michelson |

(Continued)

FOREIGN PATENT DOCUMENTS

CA 1333209 C 11/1994

(Continued)

OTHER PUBLICATIONS

Milton, AIPLA quarterly Journal, vol. 34, No. 3, p. 333-358, Summer 2006.

*Primary Examiner* — Bruce E Snow
(74) *Attorney, Agent, or Firm* — Lerner, David, Littenberg, Krumholz & Mentlik, LLP

(57) ABSTRACT

An expandable intervertebral implant and tool for use in implanting same are disclosed. The tool is useful in retaining the implant in a non-expanded state throughout insert of the implant between adjacent vertebral bodies. Among other elements, the tool includes a rod, a sleeve placed over the rod, and a locking knob attached to the rod and the sleeve to fix them with respect to each other. This construct preferably aids in preventing movement of the various components of the implant, including first and second members and first and second wedges. A method of attaching inserting the implant through the use of the tool and attaching the tool to the implant are also disclosed.

7 Claims, 20 Drawing Sheets

U.S. PATENT DOCUMENTS

| | | |
|---|---|---|
| 5,609,635 A | 3/1997 | Michelson |
| 5,653,762 A | 8/1997 | Pisharodi |
| 5,653,763 A | 8/1997 | Errico et al. |
| 5,658,335 A | 8/1997 | Allen |
| 5,665,122 A | 9/1997 | Kambin |
| 5,693,100 A | 12/1997 | Pisharodi |
| 5,702,453 A | 12/1997 | Rabbe et al. |
| 5,776,197 A | 7/1998 | Rabbe et al. |
| 5,776,199 A | 7/1998 | Michelson |
| 5,782,832 A | 7/1998 | Larsen et al. |
| 5,865,848 A | 2/1999 | Baker |
| 5,888,228 A | 3/1999 | Knothe et al. |
| 5,972,015 A | 10/1999 | Scribner et al. |
| 5,980,522 A | 11/1999 | Koros et al. |
| 6,015,436 A | 1/2000 | Schonhoffer |
| 6,039,761 A | 3/2000 | Li et al. |
| 6,080,155 A | 6/2000 | Michelson |
| 6,080,193 A | 6/2000 | Hochshuler et al. |
| 6,083,225 A | 7/2000 | Winslow et al. |
| 6,083,228 A | 7/2000 | Michelson |
| 6,090,143 A | 7/2000 | Meriwether et al. |
| 6,102,950 A | 8/2000 | Vaccaro |
| 6,113,638 A | 9/2000 | Williams et al. |
| 6,117,174 A | 9/2000 | Nolan |
| 6,127,597 A | 10/2000 | Beyar et al. |
| 6,159,244 A | 12/2000 | Suddaby |
| 6,159,245 A | 12/2000 | Meriwether et al. |
| 6,174,334 B1 | 1/2001 | Suddaby |
| 6,176,882 B1 | 1/2001 | Biedermann et al. |
| 6,183,517 B1 | 2/2001 | Suddaby |
| 6,190,414 B1 | 2/2001 | Young et al. |
| 6,193,756 B1 | 2/2001 | Studer et al. |
| 6,193,757 B1 | 2/2001 | Foley et al. |
| 6,206,923 B1 | 3/2001 | Boyd et al. |
| 6,217,579 B1 | 4/2001 | Koros |
| 6,224,604 B1 | 5/2001 | Suddaby |
| 6,245,107 B1 | 6/2001 | Ferree |
| 6,280,456 B1 | 8/2001 | Scribner et al. |
| 6,287,308 B1 | 9/2001 | Betz et al. |
| 6,302,914 B1 | 10/2001 | Michelson |
| 6,328,738 B1 | 12/2001 | Suddaby |
| 6,332,895 B1 | 12/2001 | Suddaby |
| 6,344,057 B1 | 2/2002 | Rabbe et al. |
| 6,368,351 B1 | 4/2002 | Glenn et al. |
| 6,395,031 B1 | 5/2002 | Foley et al. |
| 6,395,034 B1 | 5/2002 | Suddaby |
| 6,402,750 B1 | 6/2002 | Atkinson et al. |
| 6,409,766 B1 | 6/2002 | Brett |
| 6,432,140 B1 | 8/2002 | Lin |
| 6,436,103 B1 | 8/2002 | Suddaby |
| 6,436,140 B1 | 8/2002 | Liu et al. |
| 6,443,989 B1 | 9/2002 | Jackson |
| 6,447,544 B1 | 9/2002 | Michelson |
| 6,447,547 B1 | 9/2002 | Michelson |
| 6,451,052 B1 | 9/2002 | Burmeister et al. |
| 6,454,806 B1 | 9/2002 | Cohen et al. |
| 6,454,807 B1 | 9/2002 | Jackson |
| 6,478,823 B1 | 11/2002 | Michelson |
| 6,491,724 B1 | 12/2002 | Ferree |
| 6,527,803 B1 | 3/2003 | Crozet et al. |
| D472,632 S | 4/2003 | Anderson |
| D472,633 S | 4/2003 | Anderson |
| 6,562,074 B2 | 5/2003 | Gerbec et al. |
| 6,576,016 B1 | 6/2003 | Hochshuler et al. |
| 6,582,431 B1 | 6/2003 | Ray |
| 6,582,451 B1 | 6/2003 | Marucci et al. |
| 6,582,461 B1 | 6/2003 | Burmeister et al. |
| 6,582,467 B1 | 6/2003 | Teitelbaum et al. |
| 6,592,625 B2 | 7/2003 | Cauthen |
| 6,595,998 B2 | 7/2003 | Johnson et al. |
| 6,610,089 B1 | 8/2003 | Liu et al. |
| 6,626,905 B1 | 9/2003 | Schmiel et al. |
| 6,641,614 B1 | 11/2003 | Wagner et al. |
| 6,648,917 B2 | 11/2003 | Gerbec et al. |
| 6,685,742 B1 | 2/2004 | Jackson |
| 6,706,070 B1 | 3/2004 | Wagner et al. |
| 6,719,796 B2 | 4/2004 | Cohen et al. |
| 6,723,126 B1 | 4/2004 | Berry |
| 6,733,535 B2 | 5/2004 | Michelson |
| 6,743,255 B2 | 6/2004 | Ferree |
| 6,773,460 B2 | 8/2004 | Jackson |
| 6,814,754 B2 | 11/2004 | Greenhalgh |
| 6,821,298 B1 | 11/2004 | Jackson |
| 6,833,006 B2 | 12/2004 | Foley et al. |
| 6,835,206 B2 | 12/2004 | Jackson |
| 6,837,850 B2 | 1/2005 | Suddaby |
| 6,840,944 B2 | 1/2005 | Suddaby |
| 6,843,804 B2 | 1/2005 | Bryan |
| 6,852,129 B2 | 2/2005 | Gerbec et al. |
| 6,863,673 B2 | 3/2005 | Gerbec et al. |
| 6,875,173 B2 | 4/2005 | Suddaby |
| 6,893,464 B2 | 5/2005 | Kiester |
| 6,902,568 B2 | 6/2005 | Serhan |
| 6,953,477 B2 | 10/2005 | Berry |
| 6,955,691 B2 | 10/2005 | Chae et al. |
| 7,018,415 B1 | 3/2006 | McKay |
| 7,066,961 B2 | 6/2006 | Michelson |
| 7,070,598 B2 | 7/2006 | Lim et al. |
| 7,087,055 B2 | 8/2006 | Lim et al. |
| 7,097,648 B1 | 8/2006 | Globerman et al. |
| 7,128,760 B2 | 10/2006 | Michelson |
| D553,742 S | 10/2007 | Park |
| 7,306,626 B2 | 12/2007 | Whelan |
| 7,326,251 B2 | 2/2008 | McCombe et al. |
| 7,331,996 B2 | 2/2008 | Sato et al. |
| 7,569,074 B2 | 8/2009 | Eisermann et al. |
| 7,621,951 B2 | 11/2009 | Glenn et al. |
| 7,909,830 B2 * | 3/2011 | Frigg et al. .................. 606/86 A |
| 2001/0032020 A1 | 10/2001 | Besselink |
| 2002/0052656 A1 | 5/2002 | Michelson |
| 2002/0068974 A1 | 6/2002 | Kuslich et al. |
| 2002/0068977 A1 | 6/2002 | Jackson |
| 2002/0082696 A1 | 6/2002 | Harms et al. |
| 2002/0128716 A1 | 9/2002 | Cohen et al. |
| 2002/0138146 A1 | 9/2002 | Jackson |
| 2003/0040798 A1 | 2/2003 | Michelson |
| 2003/0065396 A1 | 4/2003 | Michelson |
| 2003/0135279 A1 | 7/2003 | Michelson |
| 2003/0149482 A1 | 8/2003 | Michelson |
| 2003/0195630 A1 | 10/2003 | Ferree |
| 2003/0208263 A1 | 11/2003 | Burmeister et al. |
| 2003/0208270 A9 | 11/2003 | Michelson |
| 2003/0208275 A1 | 11/2003 | Michelson |
| 2003/0220650 A1 | 11/2003 | Major et al. |
| 2003/0236520 A1 | 12/2003 | Lim et al. |
| 2004/0010312 A1 | 1/2004 | Enayati |
| 2004/0010315 A1 | 1/2004 | Song |
| 2004/0024463 A1 | 2/2004 | Thomas et al. |
| 2004/0030387 A1 | 2/2004 | Landry et al. |
| 2004/0044411 A1 | 3/2004 | Suddaby |
| 2004/0078080 A1 | 4/2004 | Thramann et al. |
| 2004/0087947 A1 | 5/2004 | Lim et al. |
| 2004/0087948 A1 | 5/2004 | Suddaby |
| 2004/0102774 A1 | 5/2004 | Trieu |
| 2004/0153156 A1 | 8/2004 | Cohen et al. |
| 2004/0199252 A1 | 10/2004 | Sears et al. |
| 2004/0215342 A1 | 10/2004 | Suddaby |
| 2004/0254643 A1 | 12/2004 | Jackson |
| 2004/0254644 A1 | 12/2004 | Taylor |
| 2005/0004673 A1 | 1/2005 | Kluger |
| 2005/0015149 A1 | 1/2005 | Michelson |
| 2005/0015150 A1 | 1/2005 | Lee |
| 2005/0027358 A1 | 2/2005 | Suddaby |
| 2005/0038512 A1 | 2/2005 | Michelson |
| 2005/0049590 A1 | 3/2005 | Alleyne et al. |
| 2005/0060036 A1 | 3/2005 | Schultz et al. |
| 2005/0070911 A1 | 3/2005 | Carrison et al. |
| 2005/0071007 A1 | 3/2005 | Malek |
| 2005/0113920 A1 | 5/2005 | Foley et al. |
| 2006/0022180 A1 | 2/2006 | Selness |
| 2006/0122701 A1 | 6/2006 | Kiester |
| 2006/0129244 A1 | 6/2006 | Ensign |
| 2006/0149385 A1 | 7/2006 | McKay |
| 2006/0224241 A1 | 10/2006 | Butler et al. |
| 2006/0241643 A1 | 10/2006 | Lim et al. |

| | | | | |
|---|---|---|---|---|
| 2006/0241764 A1 | 10/2006 | Michelson | | |
| 2006/0247770 A1 | 11/2006 | Peterman | | |
| 2008/0071279 A1 * | 3/2008 | Bandeira et al. ............ 606/90 | | |

FOREIGN PATENT DOCUMENTS

| | | | |
|---|---|---|---|
| EP | 0260044 A1 | 3/1988 | |
| EP | 0269175 A2 | 6/1988 | |
| EP | 0566807 A1 | 10/1993 | |
| EP | 0637439 A1 | 2/1995 | |
| EP | 0664994 A1 | 8/1995 | |
| EP | 0669114 A1 | 8/1995 | |
| EP | 0734702 A1 | 10/1996 | |
| GB | 2083754 A | 3/1982 | |
| JP | 62164458 A | 7/1987 | |
| JP | 63158045 A | 7/1988 | |
| JP | 5208029 A | 8/1993 | |
| WO | 9000037 A1 | 1/1990 | |
| WO | 9428824 A2 | 12/1994 | |
| WO | 9525485 A1 | 9/1995 | |
| WO | 9532673 A1 | 12/1995 | |
| WO | 9614809 A1 | 5/1996 | |
| WO | 9627321 A2 | 9/1996 | |
| WO | 9627345 A2 | 9/1996 | |
| WO | 9639988 A2 | 12/1996 | |
| WO | 9640015 A1 | 12/1996 | |
| WO | 9640016 A2 | 12/1996 | |
| WO | 9640019 A1 | 12/1996 | |
| WO | 9640020 A1 | 12/1996 | |
| WO | 03003951 A1 | 1/2003 | |
| WO | 2004047691 A1 | 6/2004 | |
| WO | 2004080356 A2 | 9/2004 | |
| WO | 2006034436 A2 | 3/2006 | |
| WO | 2006037013 A1 | 4/2006 | |
| WO | 2006042334 A2 | 4/2006 | |
| WO | 2006068682 A1 | 6/2006 | |
| WO | 2006116760 A2 | 11/2006 | |
| WO | 2006116761 A2 | 11/2006 | |
| WO | 2007009107 A2 | 1/2007 | |
| WO | 2007041665 A2 | 4/2007 | |

* cited by examiner

TOOL FOR IMPLANTING EXPANDABLE INTERVERTEBRAL IMPLANT

BACKGROUND OF THE INVENTION

Surgeons are performing more and more spinal surgeries to correct different spinal defects in the hopes of reducing pain and restoring normal or close to normal movement. One area of particular interest lies in the restoration of normal spacing between adjacent vertebral bodies. Whether due to the degeneration of the intervertebral disc over time or because of an injury, a decrease in spacing between vertebral bodies can cause a myriad of problems for a patient, the least of which is pain resulting from the pinching of nerves between the bodies. Correcting this problem is often very important to returning a patient to his or her normal level of activity and/or managing the pain associated with a degenerative spinal problem.

Over the years, there have been many different techniques employed in restoring the normal disc space. For instance, solid fusion devices have been implanted in many patients in the hopes of both restoring normal disc spacing and preventing further degeneration of the space by fusing the vertebral bodies to one another. Recently, there has been a trend to both restore the disc spacing and allow natural movement of the adjacent vertebral bodies with respect to one another. Nonetheless, there exist certain extreme cases of degradation of the disc space which require extreme measures in order to restore the natural spacing.

Often, the decrease in spacing will be so drastic that some amount of distraction of the adjacent vertebral bodies will be required. Although this distraction is sometimes achieved through the use of various tools, the desire for faster and more efficient surgical techniques favors the elimination of superfluous surgical steps. Thus, there exists a need for an intervertebral implant which is implantable in an unexpanded state and easily expandable to restore the disc space, thereby negating the need for additional tools and the additional surgical steps of using them.

SUMMARY OF THE INVENTION

A first aspect of the present invention is an expandable implant for implantation between two vertebral bodies. In a first embodiment of this first aspect, the implant includes a first member, the first member including a first vertebral contact surface and a first interior surface, a second member, the second member including a second vertebral contact surface and a second interior surface, the first and second interior surfaces facing towards one another, a strut attached to both the first and second members, and a wedge disposed between the first and second interior surfaces and attached to at least one of the first or second members. Preferably, in this embodiment, movement of the wedge in a first direction causes movement of at least one of the first or second members in a second direction.

In other embodiments of the first aspect, the wedge may be attached to at least one of the first or second members by a deformable tether. The implant may include first and second wedges, where movement of the first and second wedges towards one another causes an increase in a distance between the first and second interior surfaces. The first and second wedges may each be attached to both of the first and second members by a deformable tether. Additionally, one of the first or second wedges may include a bulleted or rounded surface for aiding in insertion of the expandable implant between the two vertebral bodies. Further, the first wedge may include first and second angled wedge surfaces for cooperating with first and second angled interior surfaces of the first and second members respectively, the second wedge may include third and fourth angled wedge surfaces for cooperating with third and fourth angled interior surfaces of the first and second members respectively, and movement of the first and second wedges towards one another may be permitted, while movement of the first and second wedges away from one another is prevented. This may be the case because the first, second, third, and fourth wedge surfaces and the first, second, third, and fourth interior surfaces may each include teeth. The first and second members and the first and second wedges may also cooperate to define at least one aperture through the implant adapted for bone growth therethrough.

A second aspect the present invention may be another expandable implant for implantation between two vertebral bodies. In one embodiment according to this second aspect, the implant may include a first member, the first member including a first vertebral contact surface and a first interior surface, a second member, the second member including a second vertebral contact surface and a second interior surface, the first and second interior surfaces facing towards one another, a strut attached to both the first and second members, and first and second wedges disposed between the first and second interior surfaces, one of the first or second wedges including a bulleted or rounded surface for aiding in insertion of the expandable implant between the two vertebral bodies. Preferably, in this embodiment, movement of the first wedge towards the second wedge causes an increase in a distance between the first and second interior surfaces.

In other embodiments of the second aspect, each of the first and second wedges is attached to each of the first and second members by deformable tethers. The first wedge may include first and second angled wedge surfaces for cooperating with first and second angled interior surfaces of the first and second members respectively, the second wedge may include third and fourth angled wedge surfaces for cooperating with third and fourth angled interior surfaces of the first and second members respectively, and movement of the first and second wedges towards one another may be permitted, while movement of the first and second wedges away from one another is prevented. This may be the case because the first, second, third, and fourth wedge surfaces and the first, second, third, and fourth interior surfaces each include teeth. Furthermore, the first and second members and the first and second wedges may cooperate to define at least one aperture through the implant adapted for bone growth therethrough.

A third aspect of the present invention may be another expandable implant for implantation between two vertebral bodies. According to one embodiment of this third aspect, the implant may include a first member, the first member including a first vertebral contact surface and a first interior surface, a second member, the second member including a second vertebral contact surface and a second interior surface, the first and second interior surfaces facing towards one another, a strut attached to both the first and second members, and first and second wedges disposed between the first and second interior surfaces. Preferably, in this embodiment, movement of the first wedge towards the second wedge causes an increase in a distance between the first and second interior surfaces, and at least one of the first and second wedges is prevented from torsionally moving with respect to the first and second members.

In other embodiments of the third aspect, each of the first and second wedges may be attached to each of the first and second members by deformable tethers. The first wedge may include first and second angled wedge surfaces for cooperating with first and second angled interior surfaces of the first and second members respectively, the second wedge may include third and fourth angled wedge surfaces for cooperating with third and fourth angled interior surfaces of the first and second members respectively, and movement of the first and second wedges towards one another may be permitted, while movement of the first and second wedges away from one another is prevented. This may be the case because the first, second, third, and fourth wedge surfaces and the first, second, third, and fourth interior surfaces may each include teeth. Further, the first and second members and the first and second wedges may cooperate to define at least one aperture through the implant adapted for bone growth therethrough. Still further, the first and second members may include either a depression or a protuberance, and the first and second wedges may include the other of a depression or a protuberance. The first and second members may include a tongue, a pin, or an elongate projection, and the first and second wedges may include either a groove or a channel.

A fourth aspect of the present invention is another expandable implant for implantation between two vertebral bodies. One embodiment of this fourth aspect includes a first member, the first member including a first vertebral contact surface and a first interior surface having a first and third angled interior surfaces, a second member, the second member including a second vertebral contact surface and a second interior surface having second and fourth angled interior surfaces, the first and second interior surfaces facing towards one another, a strut attached to both the first and second members, a first wedge disposed between the first and second interior surfaces, the first wedge including first and second angled wedge surfaces for cooperating with the first and second angled interior surfaces of the first and second members respectively, and a second wedge disposed between the first and second interior surfaces, the second wedge including third and fourth angled wedge surfaces for cooperating with the third and fourth angled interior surface of the first and second members respectively. Preferably, in this embodiment, movement of the first wedge towards the second wedge causes an increase in a distance between the first and second interior surfaces, and movement of the first and second wedges towards one another may be permitted, while movement of the first and second wedges away from one another is prevented.

In other embodiments of the fourth aspect, the first, second, third, and fourth wedge surfaces and the first, second, third, and fourth interior surfaces may each include teeth. Furthermore, the first and second members and the first and second wedges may cooperate to define at least one aperture through the implant adapted for bone growth therethrough.

A fifth aspect of the present invention is yet another expandable implant for implantation between two vertebral bodies. In one embodiment of this fifth aspect, the implant includes a first member, the first member including a first vertebral contact surface and a first interior surface having a first and third angled interior surfaces, a second member, the second member including a second vertebral contact surface and a second interior surface having second and fourth angled interior surfaces, the first and second interior surfaces facing towards one another, a plurality of struts attached to both the first and second members, a first wedge disposed between the first and second interior surfaces, the first wedge including first and second angled wedge surfaces for cooperating with the first and second angled interior surfaces of the first and second members respectively, a first tether connecting the first wedge to one of the first or second members, a second wedge disposed between the first and second interior surfaces, the second wedge including third and fourth angled wedge surfaces for cooperating with the third and fourth angled interior surface of the first and second members respectively, and a first tether connecting the first wedge to one of the first or second members. Preferably, in this embodiment, movement of the first wedge towards the second wedge causes an increase in a distance between the first and second interior surfaces, and the first, second, third, and fourth wedge surfaces and the first, second, third, and fourth interior surfaces each include teeth. In another embodiment, one of the first or second wedges may include a bulleted or rounded surface for aiding in insertion of the expandable implant between the two vertebral bodies.

A sixth aspect of the present invention is a method of implanting an expandable implant between two vertebral bodies. In a first embodiment of this sixth aspect, the method includes the steps of inserting the expandable implant between two vertebral bodies, the implant having a first member, a second member, and a wedge disposed between the first and second members and attached to at least one of the first or second members. The method also includes the step of moving the wedge in a first direction so as to cause movement of the first and second members in a second direction. Preferably, the moving step causes expansion of the first and second members which in turn causes movement of the vertebral bodies away from one another.

In other embodiments of the sixth aspect, the moving step may be performed through the use of a deployment tool. The inserting step may also be performed through the use of the deployment tool. In certain embodiments, the implant may further include at least one deformable strut and more than one wedge. Each wedge may be attached to at least one of the first or second members by a deformable tether, or in some cases, the wedges may be attached to both members by deformable tethers. Additionally, the implant may further include structure which allows for the movement of the at least one wedge in a first direction, but prevents movement of the wedge in an opposition direction. Furthermore, the wedge may be prevented from torsionally rotating with respect to the first and second members.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

Figure 1:
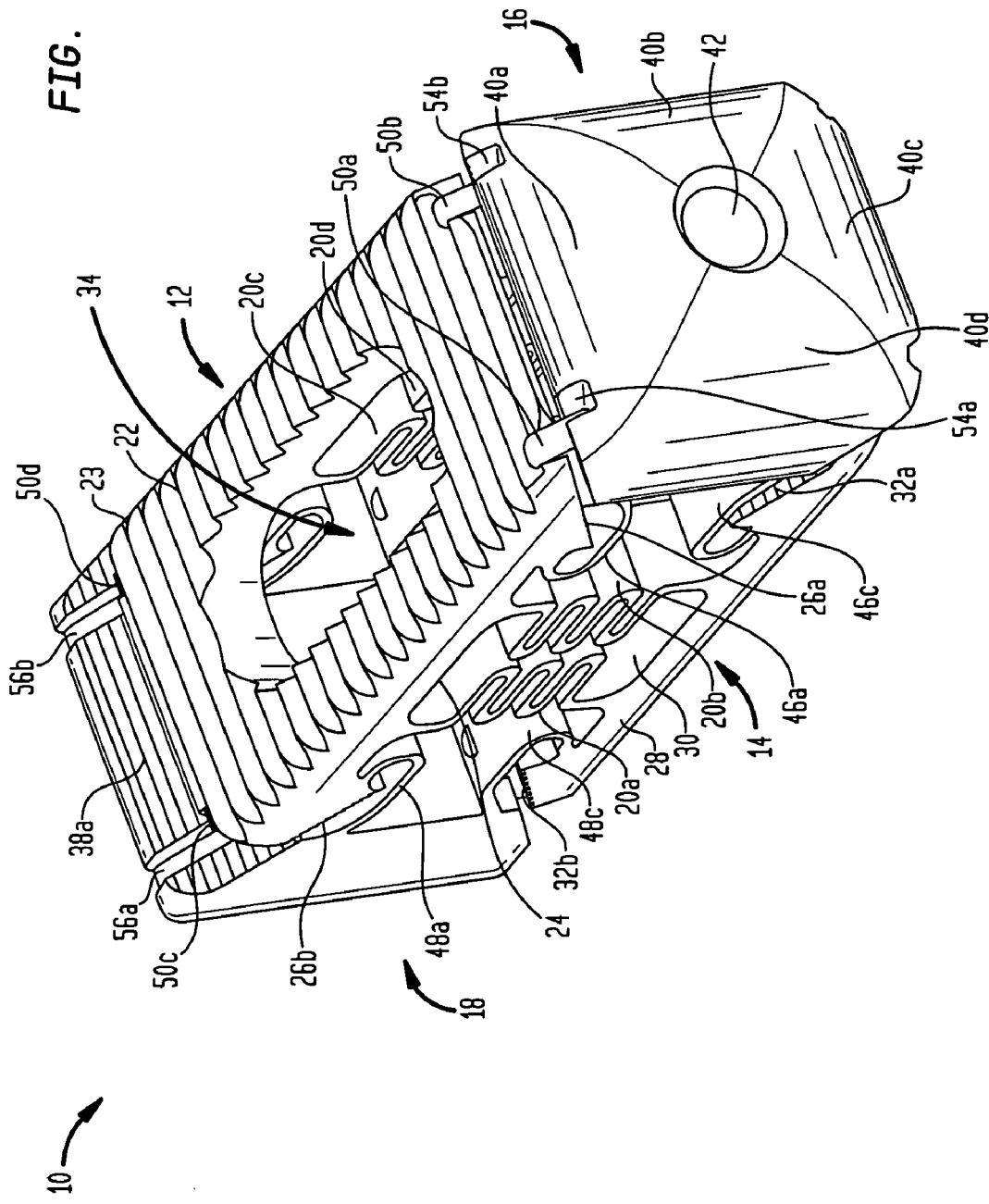
FIG. 1 is a front perspective view of an expandable intervertebral implant according to one embodiment of the present invention in a generally unexpanded state.
Figure 2:
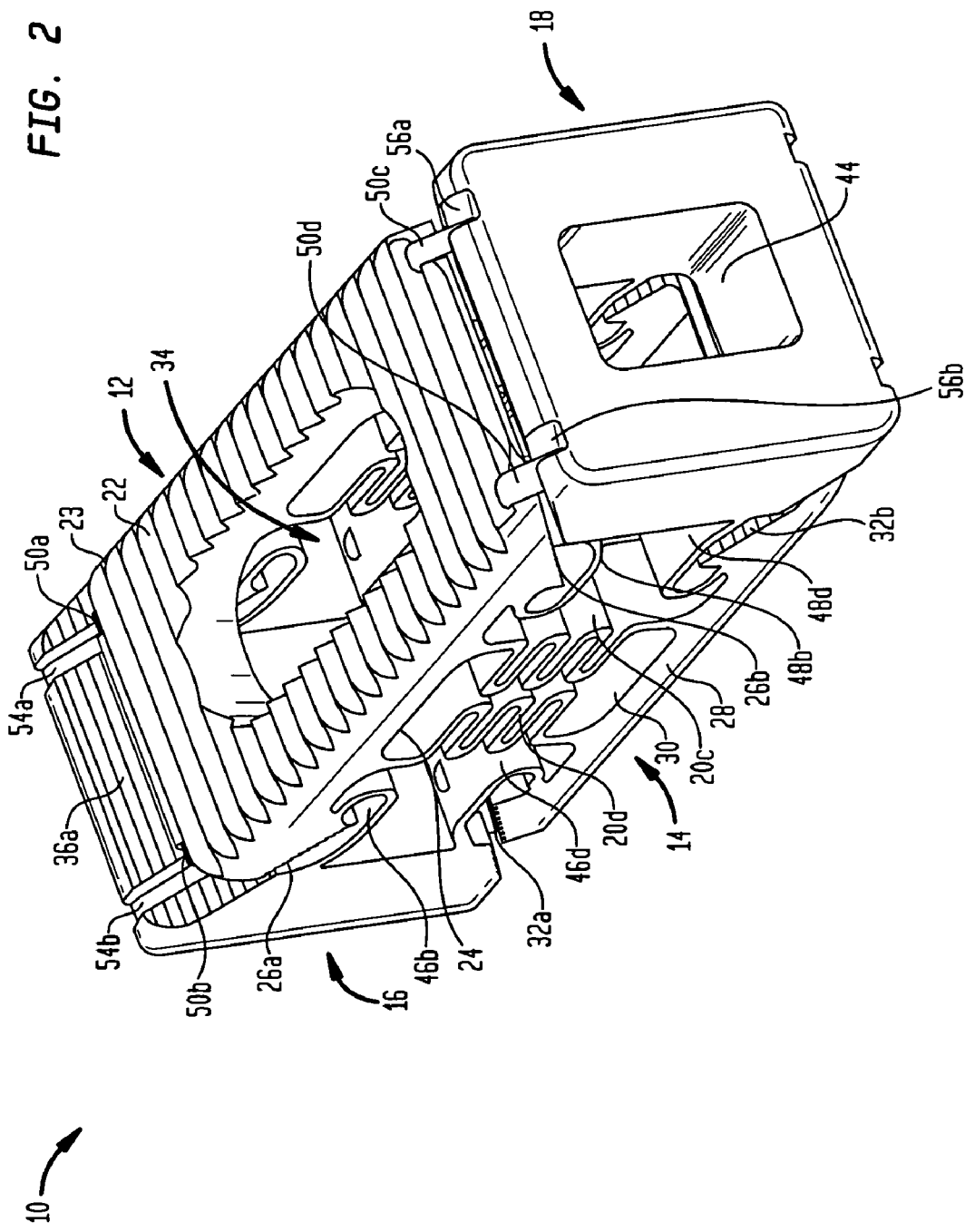
FIG. 2 is a rear perspective view of the expandable intervertebral implant shown in FIG. 1.
Figure 3:
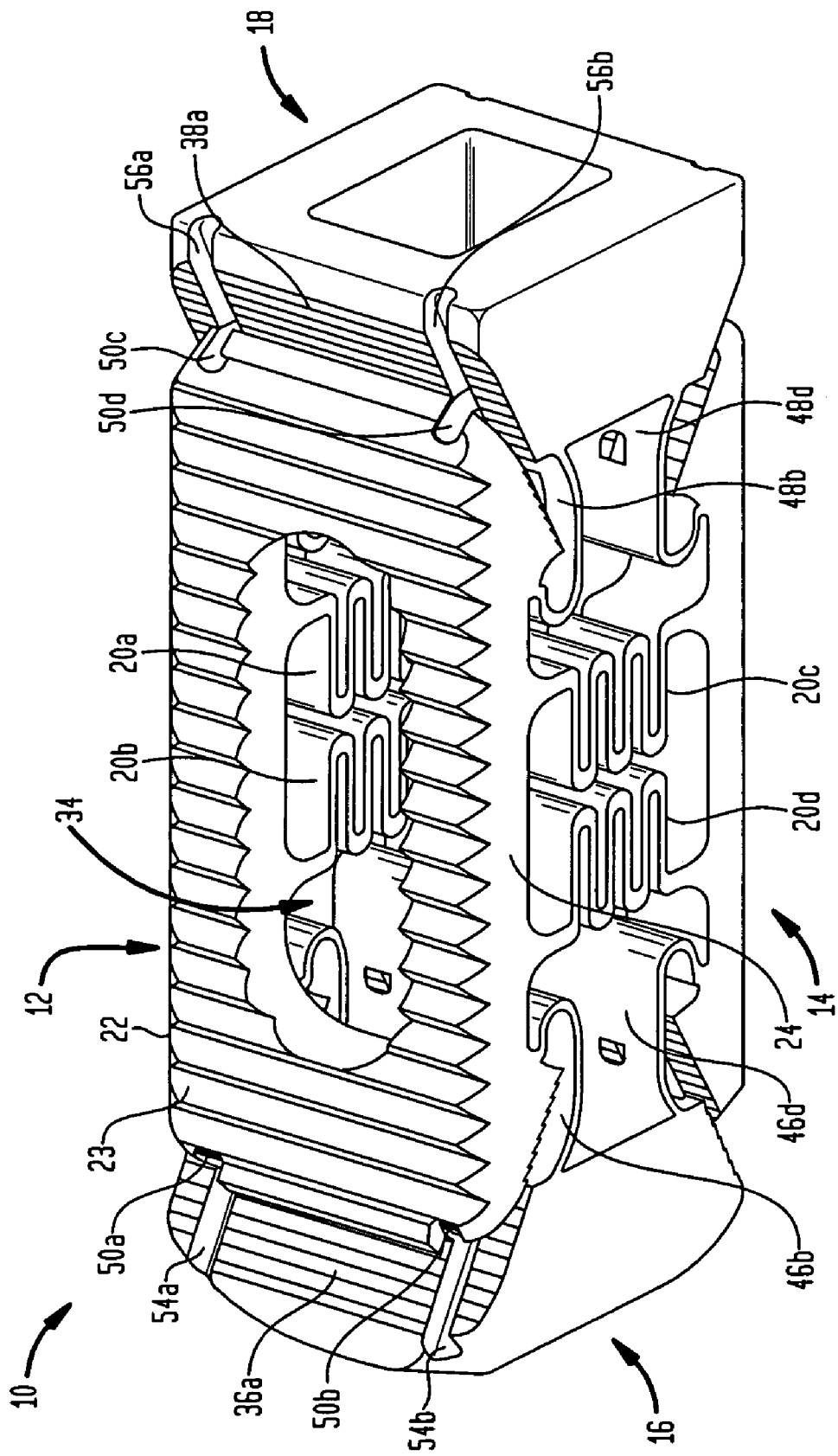
FIG. 3 is a side perspective view of the expandable intervertebral implant shown in FIG. 1.
Figure 4:
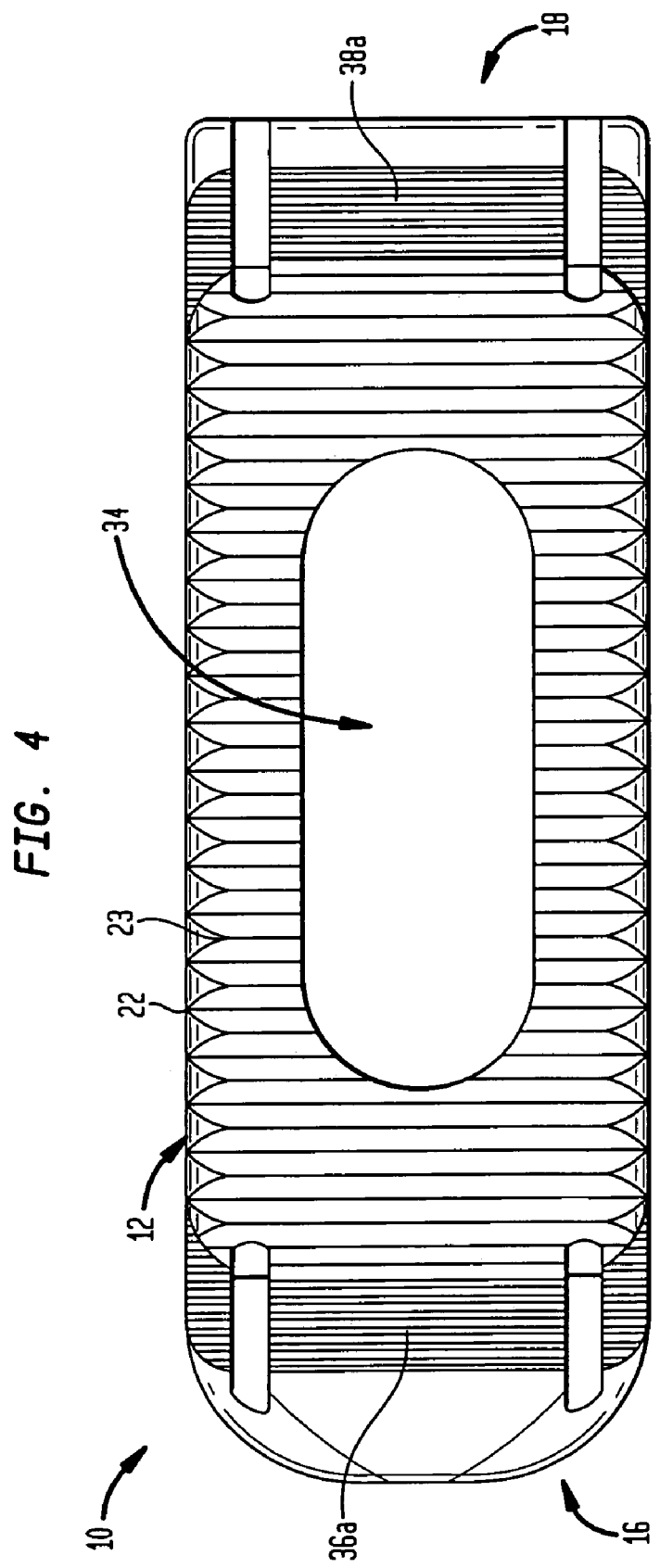
FIG. 4 is a top view of the expandable intervertebral implant shown in FIG. 1.

Referring to the drawings, wherein like reference numerals refer to like elements, FIGS. 1-6 depict a first embodiment expandable intervertebral implant, designated generally by reference numeral 10. As is shown in the drawings, implant 10 includes, among other elements that will be discussed below, a first member 12, a second member 14, a first wedge 16, a second wedge 18, and a plurality of struts 20a-d. Implant 10 is designed so that is capable of expanding from a generally unexpanded state (shown in FIGS. 1-5) to a fully expanded state (shown in FIG. 6), as well as several different partial expended states therebetween. The specific details of the structure and the operation of implant 10 will be discussed further below.

As is shown in FIGS. 1-6, first and second members 12 and 14 are generally planar plate-like elements capable of contacting and supporting a portion of vertebral bodies implant 10 is inserted between. First member 12 includes a first vertebral body contacting surface 22 and a first interior surface 24 having two first angled interior surfaces 26a and 26b. Likewise, second member includes a second vertebral body contacting surface 28 and a second interior surface 30 having two second angled interior surfaces 32a and 32b. First and second vertebral body contacting surfaces 22 and 28 may include bone engaging elements. For example, as is shown in FIGS. 1-6, first vertebral body contacting surface 22 includes projections 23 and second vertebral body contacting surface 28 includes projections 29. Preferably, these projections are capable of biting into a portion of the bone of the adjacent vertebral bodies implant 10 is inserted between. Furthermore, first angled interior surfaces 26a and 26b may include teeth 27a and 27b, respectively, while second angled interior surfaces 32a and 32b may include teeth 33a and 33b, respectively. Finally, first member 12 may define a first aperture 34 and second member 14 may define a second aperture 35 (only partially shown).

Figure 5:
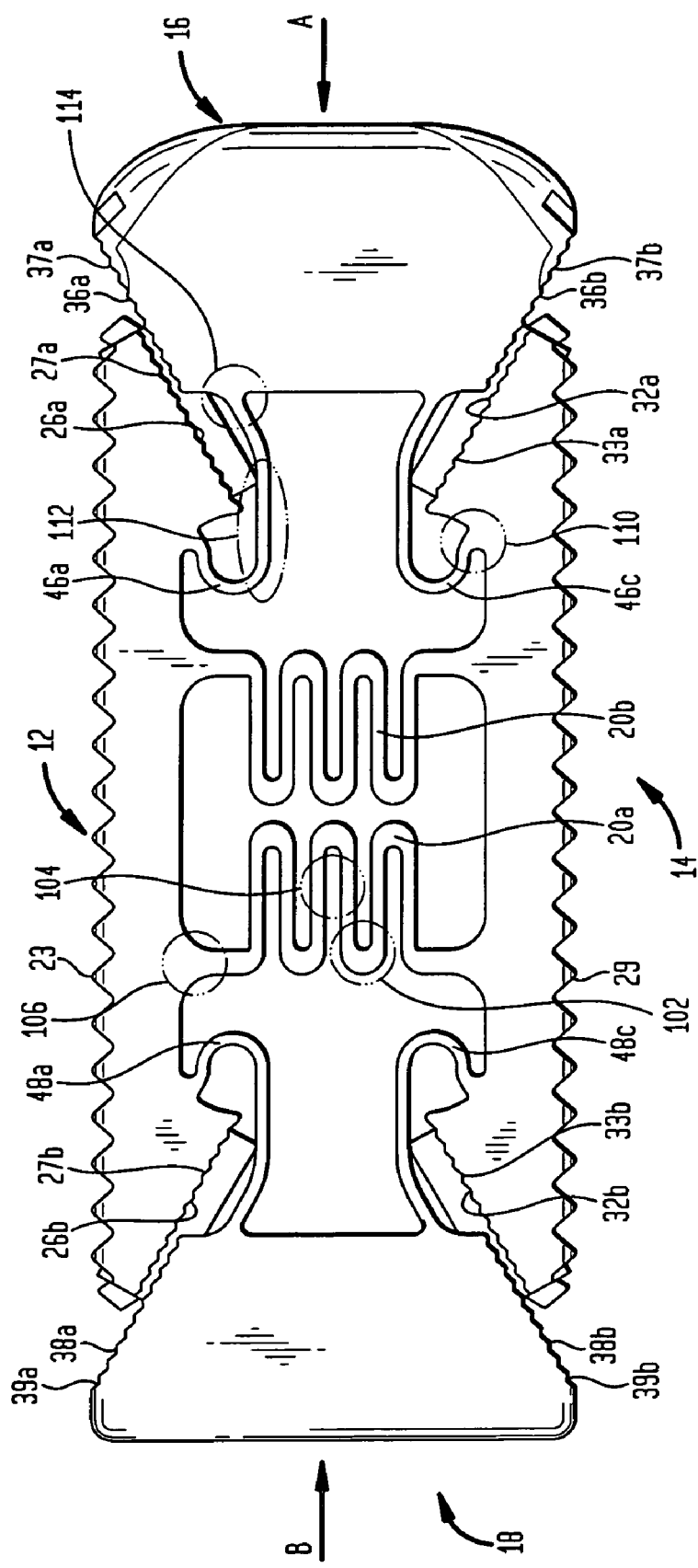
FIG. 5 is a side view of the expandable intervertebral implant shown in FIG. 1.

As is also shown in FIGS. 1-6, first and second wedges 16 and 18 are somewhat triangular and include surfaces capable of cooperating with the above-discussed first and second angled interior surfaces. Specifically, first wedge 16 includes first and second angled wedge surfaces 36a and 36b for cooperation with first angled interior surface 26a and second angled interior surface 32a, and second wedge 18 includes third and fourth angled wedge surfaces 38a and 38b for cooperation with first angled interior surface 26b and second angled interior surface 32b. The various wedge surfaces may include similar teeth to those discussed above in connection with first and second angled interior surfaces. For instance, as is best shown in FIGS. 5, first and second angled wedge surfaces 36a and 36b include teeth 37a and 37b, respectively, and third and fourth angled wedges surfaces 38a and 38b include teeth 39a and 39b, respectively. The different cooperating teeth (i.e., 27a and 37a, 27b and 39a, 33a and 37b, and 33b and 39b) preferably allow for movement of first and second wedges 16 and 18 with respect to first and second members 12 and 14 in one direction, but prevent it in an opposite direction. This will be discussed further below. It is to be understood that the wedges may exhibit any shape suitable for use in expansion of implant 10.

First wedge 16 may further include an angled, bulleted, or rounded exterior surface for aiding in insertion of implant 10 between adjacent vertebrae. In the embodiment shown in FIGS. 1-6, first wedge 16 includes rounded exterior surfaces 40a-d, which provides the bulleted nature of the exterior to the element. However, it is to be understood that angled surfaces may also be employed to achieve essentially the same functionality. First wedge 16 also preferably includes a first wedge aperture 42 (best shown in FIG. 1) formed therethrough and second wedge 18 preferably includes a second wedge aperture 44 (best shown in FIG. 2) formed therethrough. Both of these additional elements are preferably provided for use during expansion of implant 10, as will be discussed further below.

Struts 20a-d are preferably deformable so as to allow for the expansion of implant 10 upon the movement of first and second members 12 and 14 away from one another. There are many different designs for such deformable struts that may be employed. For example, as is shown in FIGS. 1-6, struts 20a-d are of an s-curve shape which facilitate easy compression and expansion. In addition, struts 20a-d are preferably designed so that they apply tension to first and second members 12 and 14 during and after expansion of implant 10. This encourages even deployment of the device. More particularly, each of struts 20a-20d incorporates a specific structure designed to aid in the movement in first and second members 12 and 14 away from one another. As is shown in FIG. 5, each of the struts (of which only struts 20a and 20b are shown in FIG. 5) includes at least one curved section 102, which is designed to be thicker than at least one middle section 104, such that the curved section 102 will deform subsequent to the deformation of middle section 104. Furthermore, each strut preferably includes at least one end section 106 that is joined to one of end plates 12 and 14. This end section 106 is preferably designed in a thicker fashion, such that there is no deformation at this point at anytime during the entire expansion sequence. Thus, the specific configuration of struts 20a-d facilitates the even deployment of implant 10 by specifically providing a structure that allows for a predetermined and consistent expansion sequence.

Figure 6:
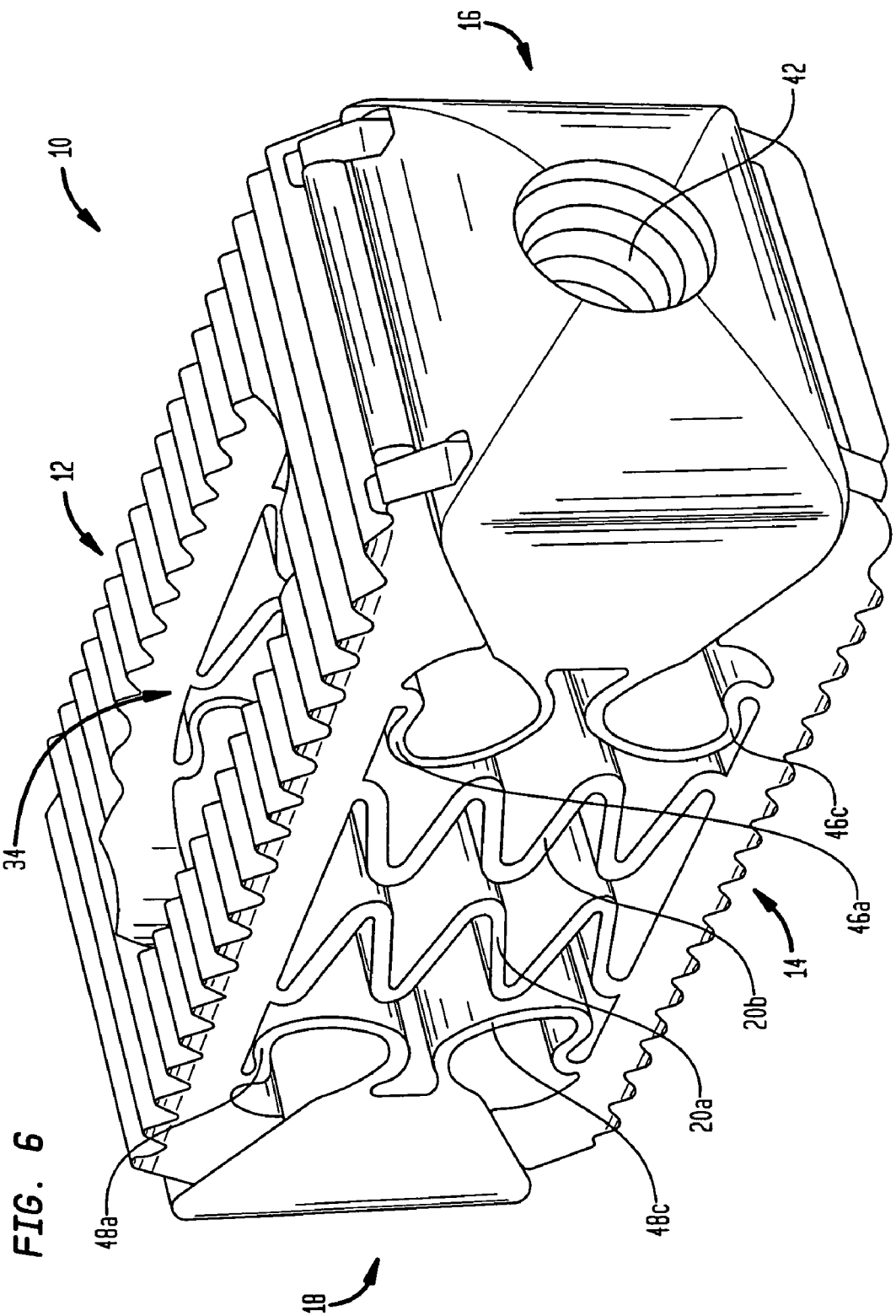
FIG. 6 is a front perspective view of the expandable intervertebral implant shown in FIG. 1 in a fully expanded state.

First and second wedges 16 and 18 are each respectively attached to both first and second members 12 and 14. As is shown in FIGS. 1-6, first wedge 16 is attached to first member 12 through the use of tethers 46a and 46b, and to second member 14 through the use of tethers 46c and 46d. Likewise, second wedge 18 is attached to first member 12 through the use of tethers 48a and 48b, and to second member 14 through the use of tethers 48c and 48d. Of course, any number of tethers may be utilized in connecting the wedges to the first and second members. Tethers 46a-d and 48a-d are preferably deformable so as to allow the movement of first and second wedges 16 and 18 with respect to first and second members 12 and 14. As is shown in the figures, the tethers may employ a shape that allows them to deform in a proper fashion upon movement of first and second wedges 16 and 18 with respect to first and second members 12 and 14. Like struts 20a-d, tethers 46a-d and 48a-d incorporate a structure specifically designed to allow for an even and consistent deployment of implant 10. Specifically, each tether includes an end section 110 (best shown in connection with the illustration of tethers 46a, 46c, 48a, and 48c in FIG. 5) at the connection between the tether and one of first or second members 12 or 14, which is thicker than other areas of the tether to limit deformation. In addition, this section 110 is shaped in the manner shown in order to force a thinner curved tether section 112 to deform toward either the first or second member during the initial expansion of implant 10. This specific geometry results in the tether's initial movement to be a collapsing motion at section 110. Furthermore, each of tethers 46a-d and 48a-d include a connection section 114 at the connection between the tether and one of first or second wedges 16 or 18. This section, like section 110, is thicker than section 112 to limit the amount of deformation at the coupling of the tether and the wedge. The final expanded state of implant 10 is best shown in FIG. 6, which illustrates the final position of the tethers.

In order to be suitable for implantation into the human body, all of the elements of implant 10 are preferably biocompatible. For example, in a preferred embodiment, each of the components of implant 10 is constructed of a metal, such as titanium (commercially pure grade 2). However, other biocompatible materials may be utilized, like other titaniums, PEEK, titanium/PEEK composites, nitonol, bioresorbables, and the like. Depending upon the material utilized, certain of the components may be formed integral with or separately from one another. For example, struts 20a-d, in certain embodiments, may be formed integral with first and second members 12 and 14. Of course, in other embodiments, struts 20a-d and first and second members 12 and 14 may be formed separately and constructed together in accordance with normal practices. For instance, these portions could be welded or otherwise fused together.

Implant 10 also preferably includes certain elements which cooperate to substantially prevent torsional movement of the first and second wedges 16 and 18 with respect to first and second members 12 and 14. Of course, such elements are not required for proper operation of the device. As is shown in FIGS. 1-6, first and second members 12 and 14 are provided with elongate protuberances (50a-d and 52a-d, respectively). These protuberances preferably extend somewhat below the angled interior surfaces of first and second members 12 and 14, respectively. First and second wedges 16 and 18, on the other hand, each include four channels for cooperation with the protuberances. Specifically, first wedge includes channels 54a-d and second wedge includes channels 56a-d.

The cooperation between the above-discussed protuberances and channels is such that movement of wedges 16 and 18 with respect to each other and first and second members 12 and 14 is not inhibited (i.e., the wedges can move in similar directions as depicted by arrows A and B of FIG. 5). However, any torsional or rotational movement of the wedges with respect to the first and second members is prevented. In other words, first and second wedges 16 and 18 are prevented from going off track. This is an important feature in ensuring a consistent operation of implant 10.

In operation, movement of first wedge 16 in the direction of arrow A (FIG. 5) and movement of second wedge 18 in the direction of arrow B (also FIG. 5), causes first and second members 12 and 14 to move away from one another. In other words, movement of first and second wedges 16 and 18 towards one another causes the expansion of implant 10. Movement of first and second wedges 16 and 18 can be achieved through the use of a deployment tool (discussed below). At least a portion of such a tool preferably passes through second wedge aperture 44 of second wedge 18, through an interior of implant 10 defined by first and second members 12 and 14 and struts 20a-d, and into engagement with first wedge aperture 42. In certain embodiments, first wedge aperture 42 is threaded so as to allow for threadable engagement of the tool to the first wedge. However, other connections may also be utilized. As is discussed more fully below, deployment tool preferably acts so as to apply a pushing force to second wedge 18 while at the same time applying a pulling force to first wedge 16. This causes the necessary movement of the first and second wedges 16 and 18 towards one another.

The deformable nature of tethers 46a-d and 48a-d allows them to follow along with first and second wedges 16 and 18 during their movement towards one another. So, at all times the wedges are connected to first and second members 12 and 14, thereby preventing them from becoming dislodged from implant 10. This is an important safety feature of the implant. Furthermore, the above-discussed teeth located on the first and second angled interior surfaces and the angled wedge surfaces allows for the movement of first and second wedges 16 and 18 in the direction of arrows A and B, respectively, but prevents opposite movement of the components. In other words, the different cooperating teeth (i.e., 27a and 37a, 27b and 39a, 33a and 37b, and 33b and 39b) are designed so as to allow the first movement, but prevent the second, opposite movement. Many different teeth designs can be employed in order to achieve this functionality.

Figure 13:
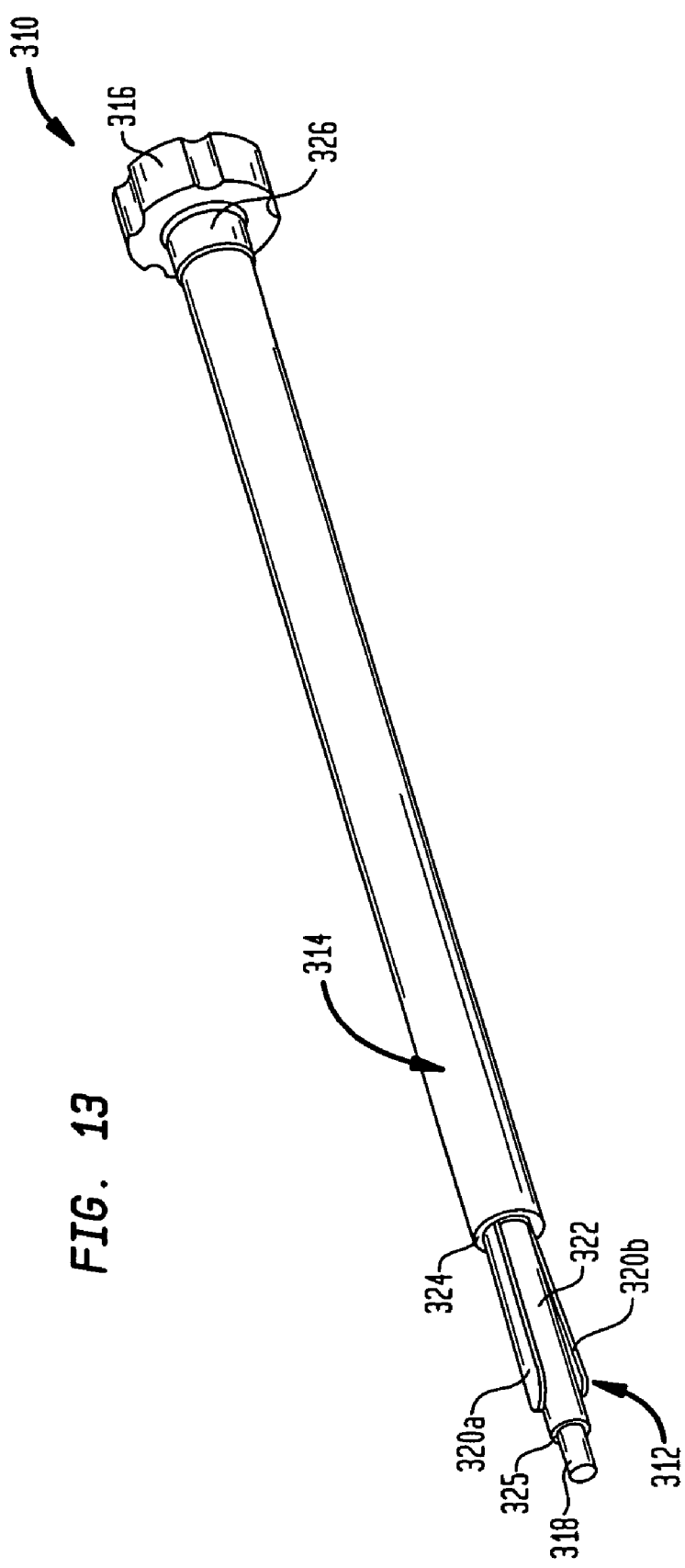
FIG. 13 is a perspective view of an impaction instrument for use with the expandable intervertebral implant shown in FIG. 1.
Figure 14:
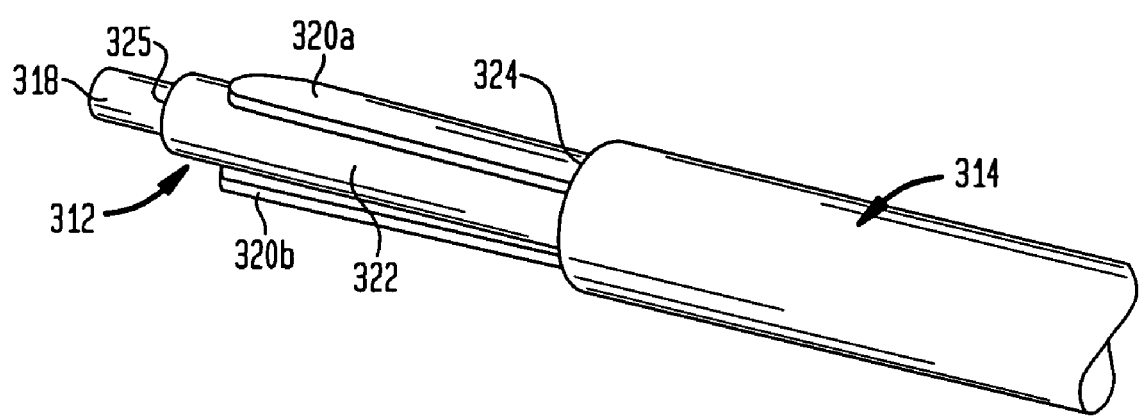
FIG. 14 is an enlarged view of a distal portion of the impaction instrument shown in FIG. 13.
Figure 15:
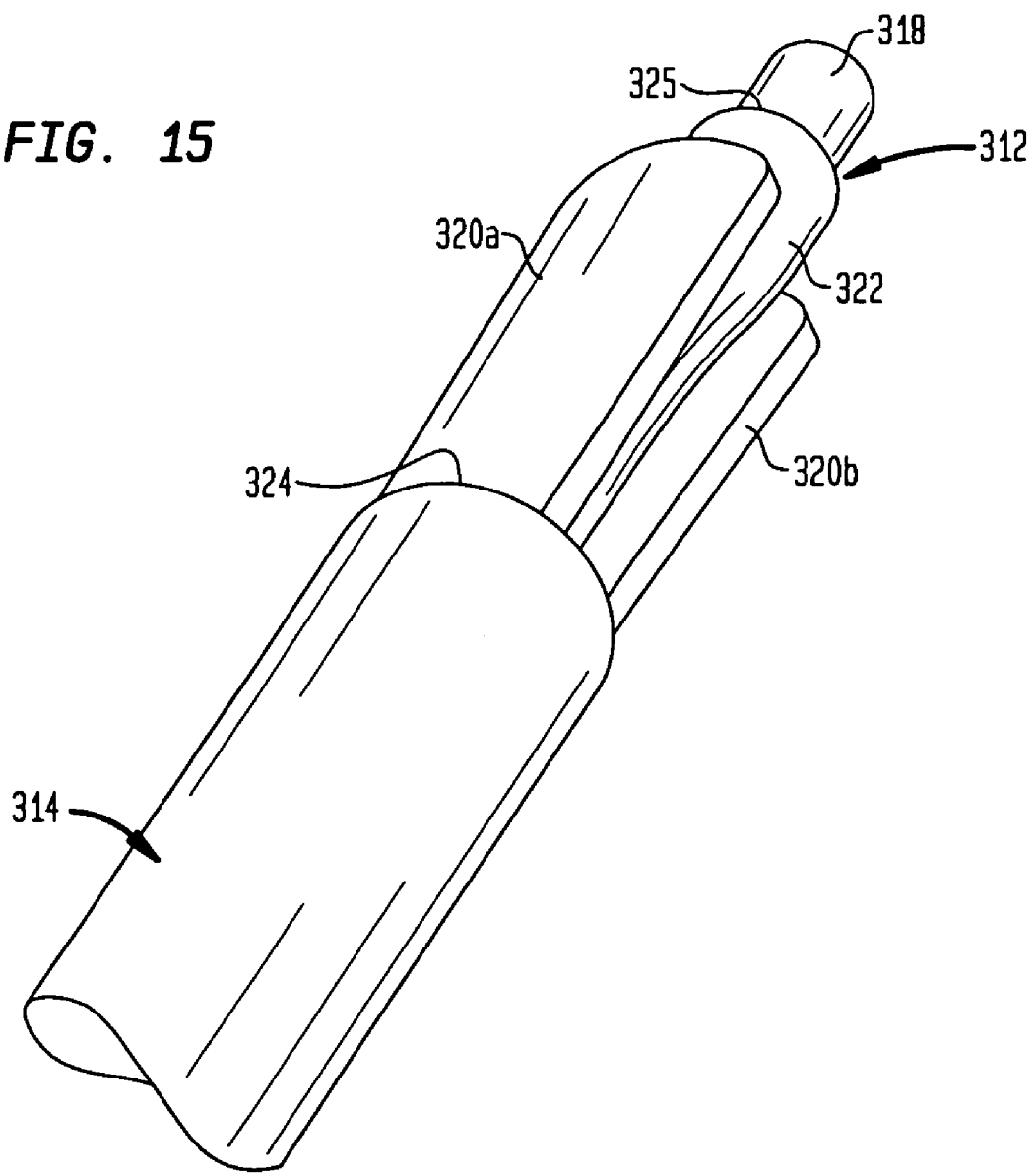
FIG. 15 is another enlarged view of the distal end of the impaction instrument shown in FIG. 13.

FIGS. 13-19 depict an impaction instrument 310. This instrument is preferably utilized by a surgeon or other medical professional in order to initially place the implant between two adjacent vertebral bodies. Because of the nature of a damaged intervertebral disc space (i.e., in a collapsed position), even the nonexpanded state of implant 10 may be slightly larger than the space between adjacent vertebral bodies. Thus, an impaction instrument, like instrument 310, often must be utilized in initially placing implant 10 in position. As is shown in FIGS. 13-19, instrument 310 includes three separate components, a tapered rod 312, a sleeve 314, and a locking knob 316. Tapered rod 312 is preferably threaded at its distal end 318 in order to couple with a portion of implant 10. In other embodiments, different coupling mechanisms may be employed. Sleeve 314 preferably includes a pair of deformable fingers 320a and 320b, which are capable of expanding outwardly upon insertion of sleeve 314 over the tapered portion 322 of tapered rod 312. This expanded state is best shown in FIGS. 13-15.

Figure 16:
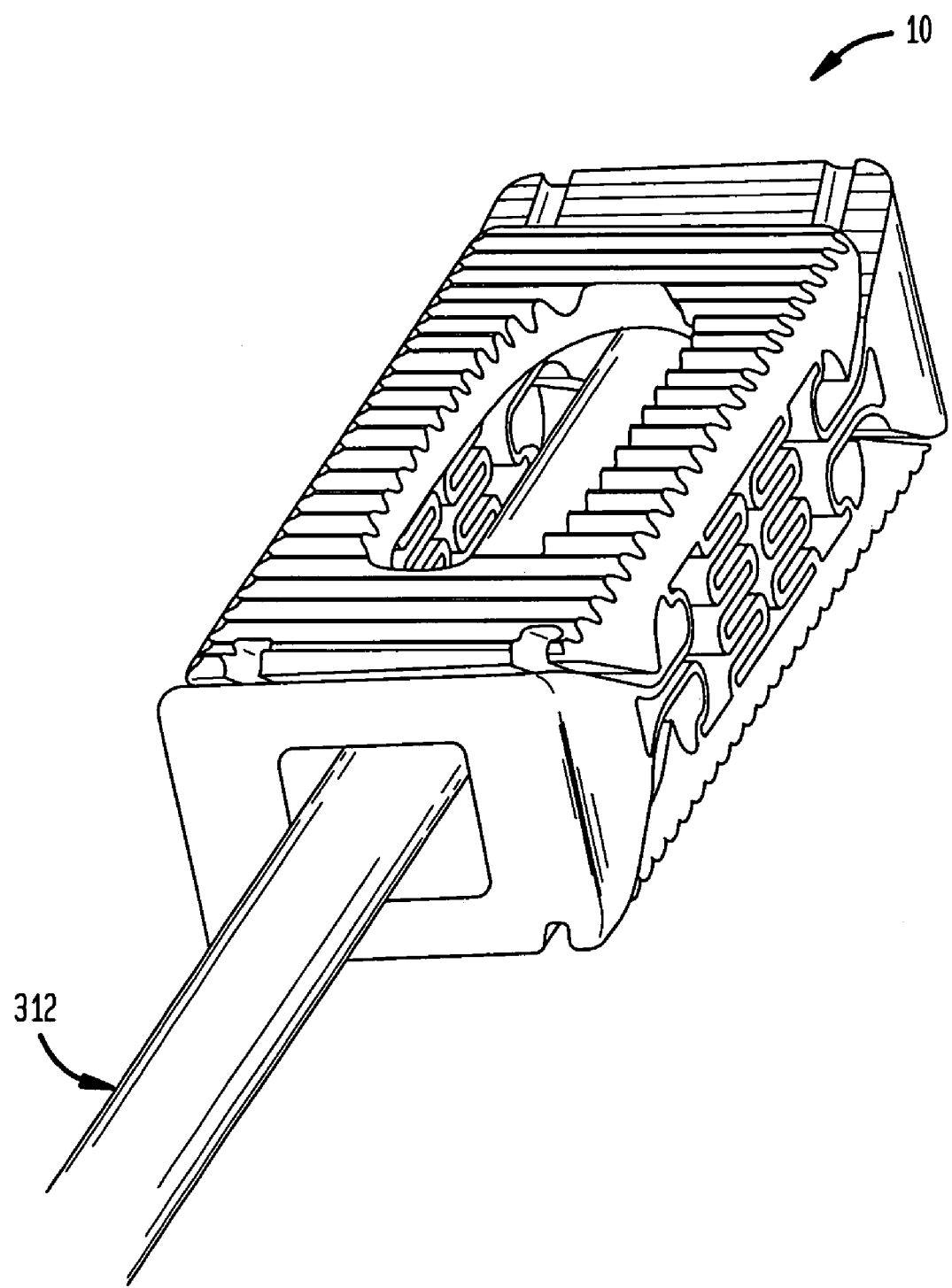
FIG. 16 is a perspective view of a portion of one end of the impaction instrument shown in FIG. 13, assembled with the expandable intervertebral implant shown in FIG. 1.
Figure 17:
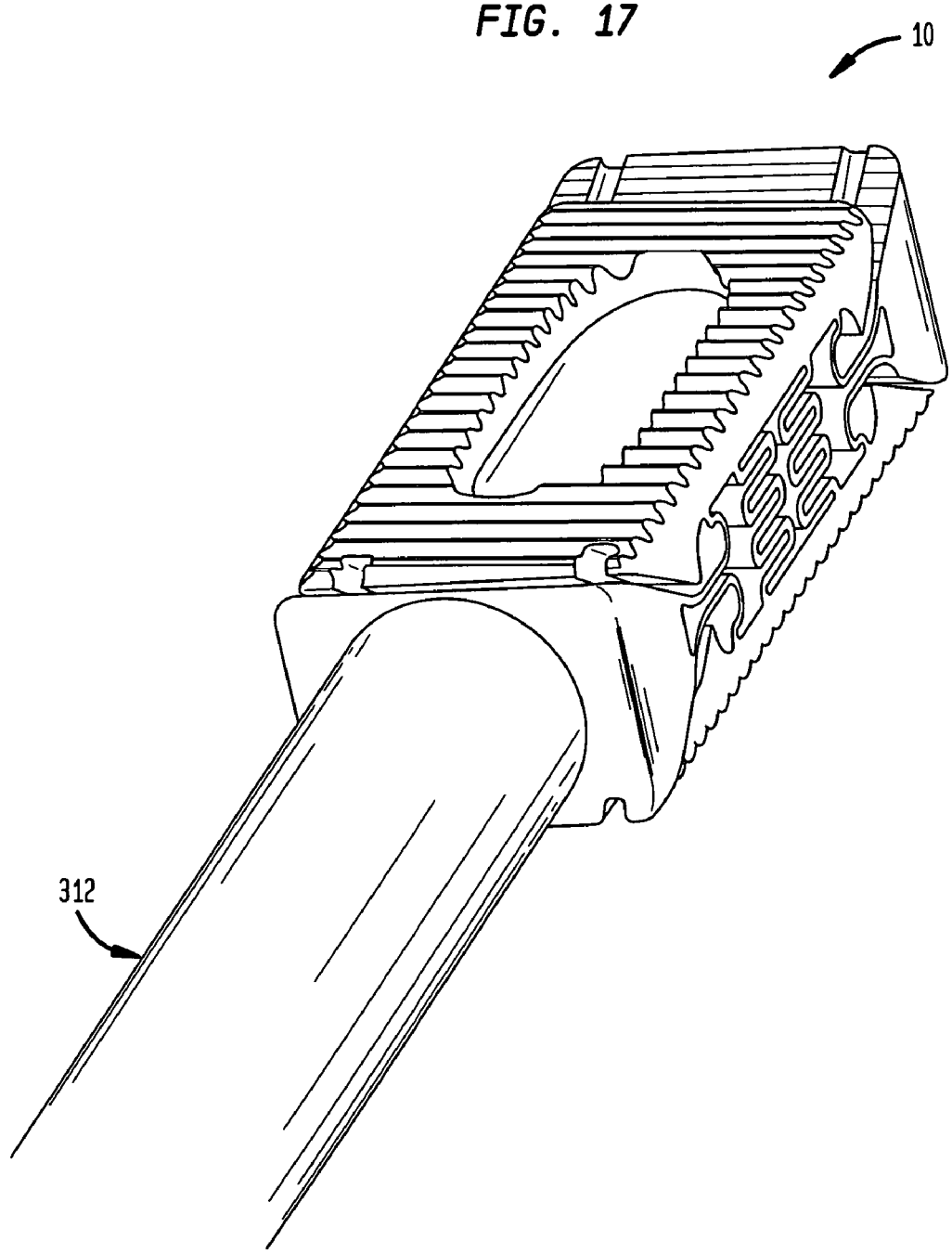
FIG. 17 is a perspective view of one end of the impaction instrument shown in FIG. 13, fully assembled with the expandable intervertebral implant shown in FIG. 1.
Figure 18:
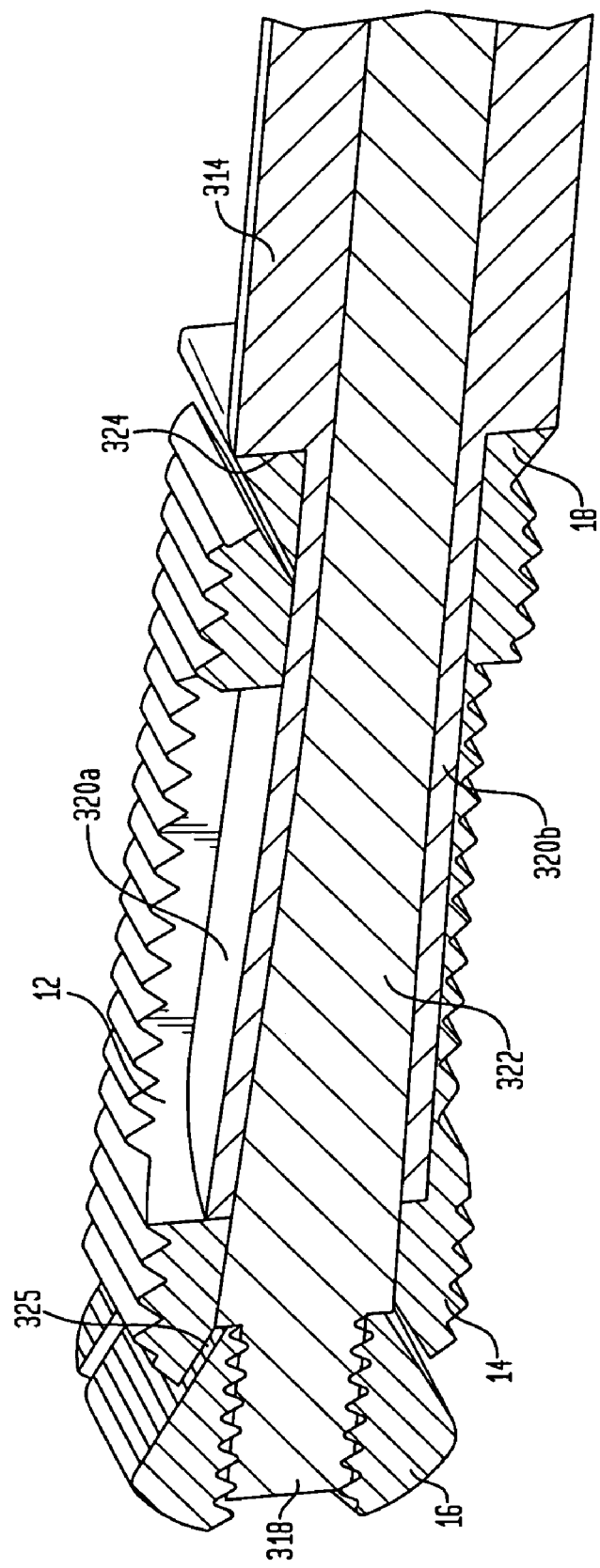
FIG. 18 is a side cross-sectional view of the assembly shown in FIG. 17.
Figure 19:
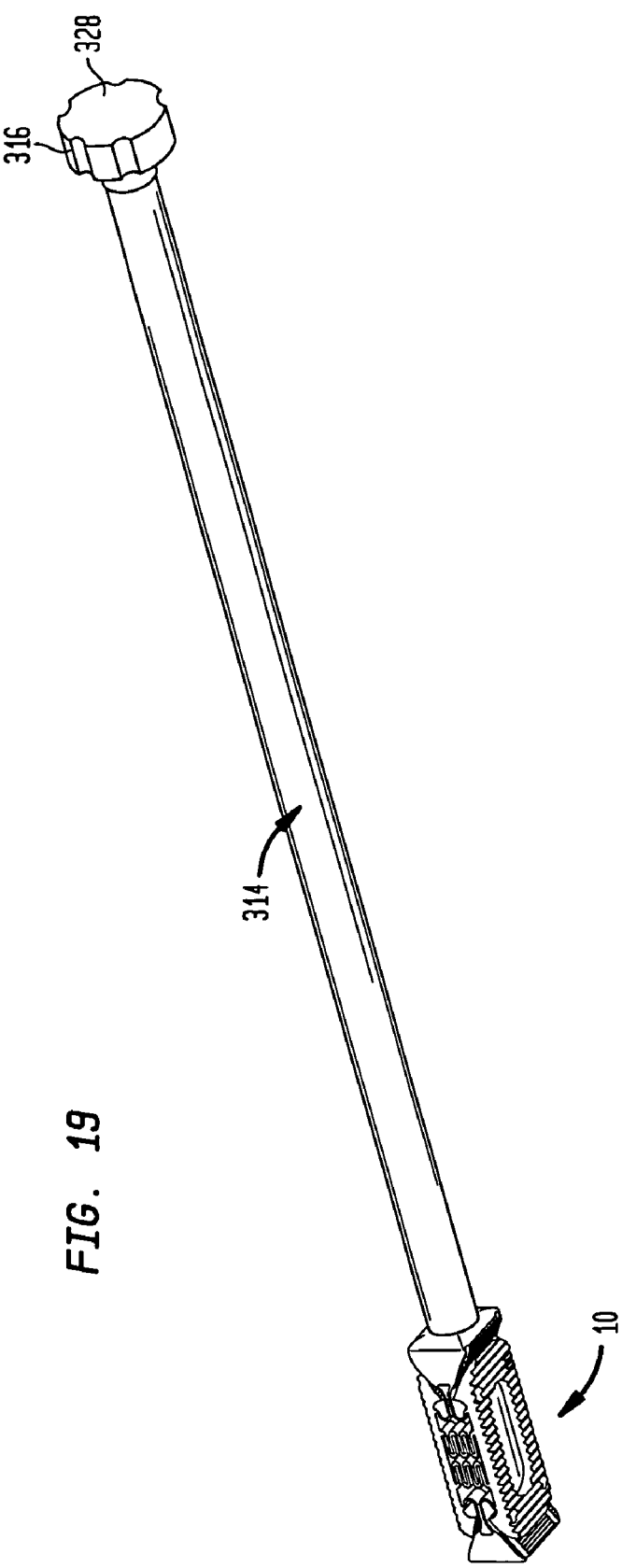
FIG. 19 is a perspective view of the impaction instrument shown in FIG. 13, fully assembled with the expandable intervertebral implant shown in FIG. 1.

In use of instrument 310, a surgeon would first couple tapered rod 312 with implant 10, by passing distal end 318 of the rod through aperture 44 in the wedge 18 and into contact with aperture 42 of first wedge 16. At this time, the threadable connection can be made by simply threading distal portion into aperture 42. The general coupling of rod 312 with implant 10 is best shown in FIG. 16, while FIG. 18 depicts the threadable coupling of the distal end of rod 312 with aperture 42 of first wedge 16. Once the position shown in FIG. 16 is achieved, a surgeon or other medical professional then preferably slides sleeve 314 over tapered rod 12, thereby expanding fingers 320a and 320b. This state is best shown in FIG. 17. As is shown in the cross sectional view of FIG. 18, fingers 320a and 320b contact a portion of each of first and second members 12 and 14. In addition, as sleeve rod 314 is inserted over tapered rod 312, a shoulder portion 324 of such is engaged with an exterior portion of second wedge 18. At the same time, distal end 318 of rod 312 is engaged with aperture 42 of wedge 16 and a shoulder portion 325 of rod 312 is in contact with a surface of wedge 16. In this position, locking knob 316 is then tightened down on the proximal end 326 of instrument 310, thereby locking rod 312 and sleeve 314 in position. Implant 10 is now protected for insertion through impaction, as first and second members 12 and 14, and wedges 16 and 18 are locked in position and cannot move with respect to each other or any other component of this assembly. A hammer or other impaction instrument can be utilized to apply a force to a back portion 328 (best shown in FIG. 19) of locking knob 316 in order to push implant 10 into the intervertebral disc space. In this regard, it is to be understood that portion 328 may be provided with a coating or other material suitable to accept the shock provided by the force from a hammer or the like.

Figure 20:
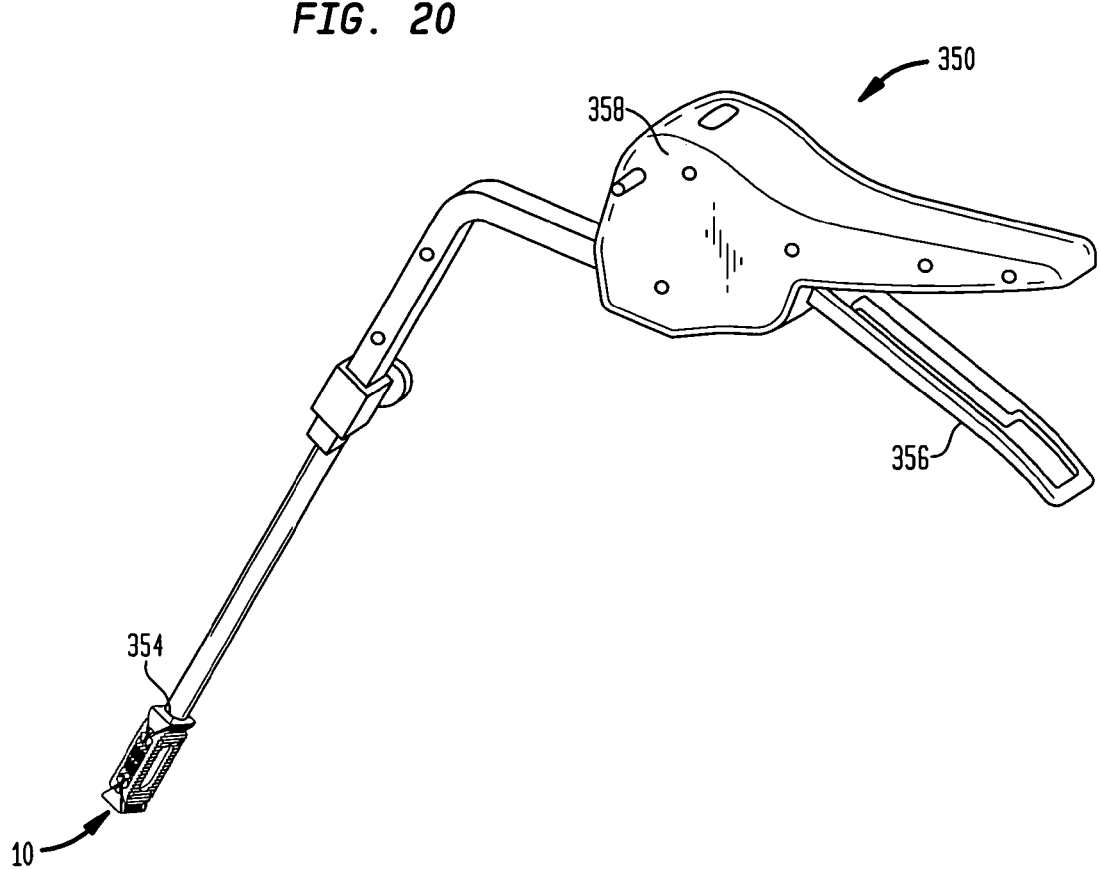
FIG. 20 is a perspective view of a deployment tool coupled with the intervertebral implant shown in FIG. 1.

FIG. 20 shows a sample deployment tool 350. As is mentioned above, such tool includes a distal portion 352 (shown being disposed within implant 10) capable of passing through aperture 44 of second wedge 18 and into engagement with aperture 42 of first wedge 16. In addition, tool 350 also includes a portion 354 capable of engagement with second wedge 18. Upon actuation of a trigger 356, first portion 352 and second portion 354 move toward one another, thereby pushing wedges 16 and 18 toward one another. This movement of first and second portion 352 and 354 towards one another is facilitated by an actuation mechanism 358 associated with trigger 356. As is more fully discussed above, this movement leads to the expansion of implant 10. Although the embodiment shown includes a first portion, which is designed to threadably connect with aperture 42, other connections are clearly contemplated.

During a surgical procedure, a surgeon would preferably insert an unexpanded implant 10 into the space between two adjacent vertebra, utilizing the above-discussed impaction instrument 310. This space would preferably first be cleared so as to provide the space necessary to receive the implant. The angled, bulleted, or rounded exterior surface of first wedge 16 is preferably first inserted thereby aiding in the complete insertion of implant 10. These surfaces essentially make insertion easier, and may facilitate a slight distraction of the adjacent vertebra in order to allow for acceptance of implant 10 into the space. Impaction instrument 310 preferably holds the various components of implant 10 in a locked position throughout the insertion. Once fully inserted between the adjacent vertebrae, deployment tool 350 may be engaged with implant 10. It is to be understood that while insertion and deployments of the implant can be achieved through the use of two different tools, it is also possible to utilize a single tool for both steps. For example, a combination impaction and deployment tool (not shown) could be provided and engaged with implant 10 prior to insertion and left attached throughout deployment.

Upon movement of first and second wedges 16 and 18 towards one another, first and second members 12 and 14 expand, which preferably acts to both distract the vertebral space and also dig projections 23 and 29 of the vertebral contact surfaces 22 and 28 into the vertebral end plates of the vertebra they are in contact with. As is mentioned above, the different cooperating teeth (i.e., 27a and 37a, 27b and 39a, 33a and 37b, and 33b and 39b) allow for the expansion of implant 10, but prevent its contraction. Thus, once expanded, implant 10 remains in such a state without the addition of any further components. Nonetheless, one or more locking components could be utilized to ensure that implant 10 remains in the expanded state.

It is to be understood that the above brief discussion of the surgical procedure associated with the present invention is merely exemplary, and more, less, or different steps may be performed. Moreover, it is to be understood that more than one implant 10 may be inserted and deployed between adjacent vertebrae. Depending upon the overall size of the implant (which may widely vary), more than one implant may be required in order to properly support the disc space. With the implant(s) in place and deployed, the disc space is preferably restored to at or near its original height. Bone growth may preferably occur through apertures 34 and 36 of the first and second members 12 and 14, respectively. It is noted that first and second wedges 12 and 14 may include similar apertures or voids which ensure an open passage through implant 10 upon full expansion. In the expanded state, the interior of implant 10 can be packed with bone morphonogenic proteins or other bone growth inducing substances in order to encourage this bone growth from one adjacent vertebra to the other.

Figure 7:
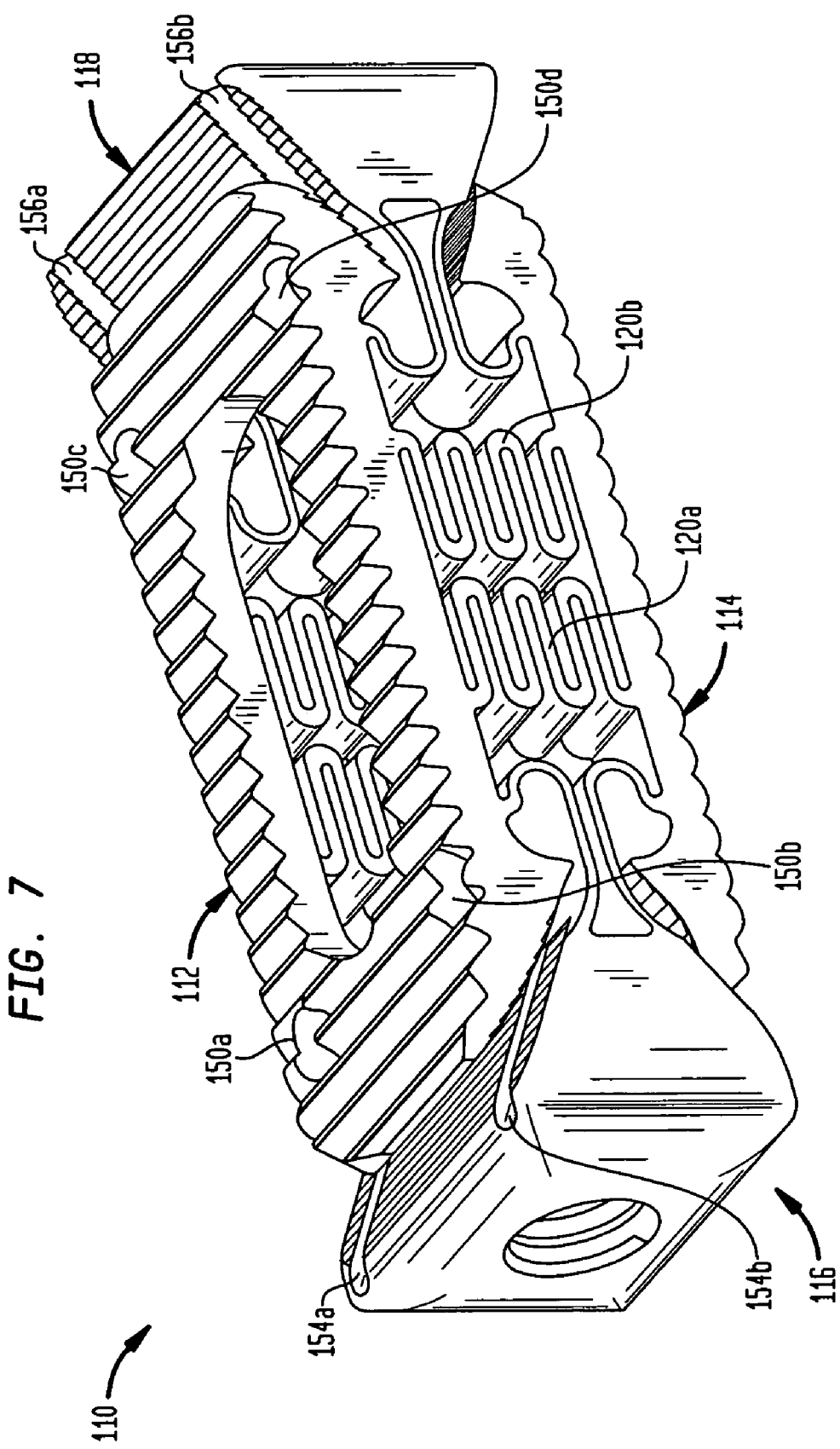
FIG. 7 is a perspective view of an expandable intervertebral implant according to another embodiment of the present invention.
Figure 8:
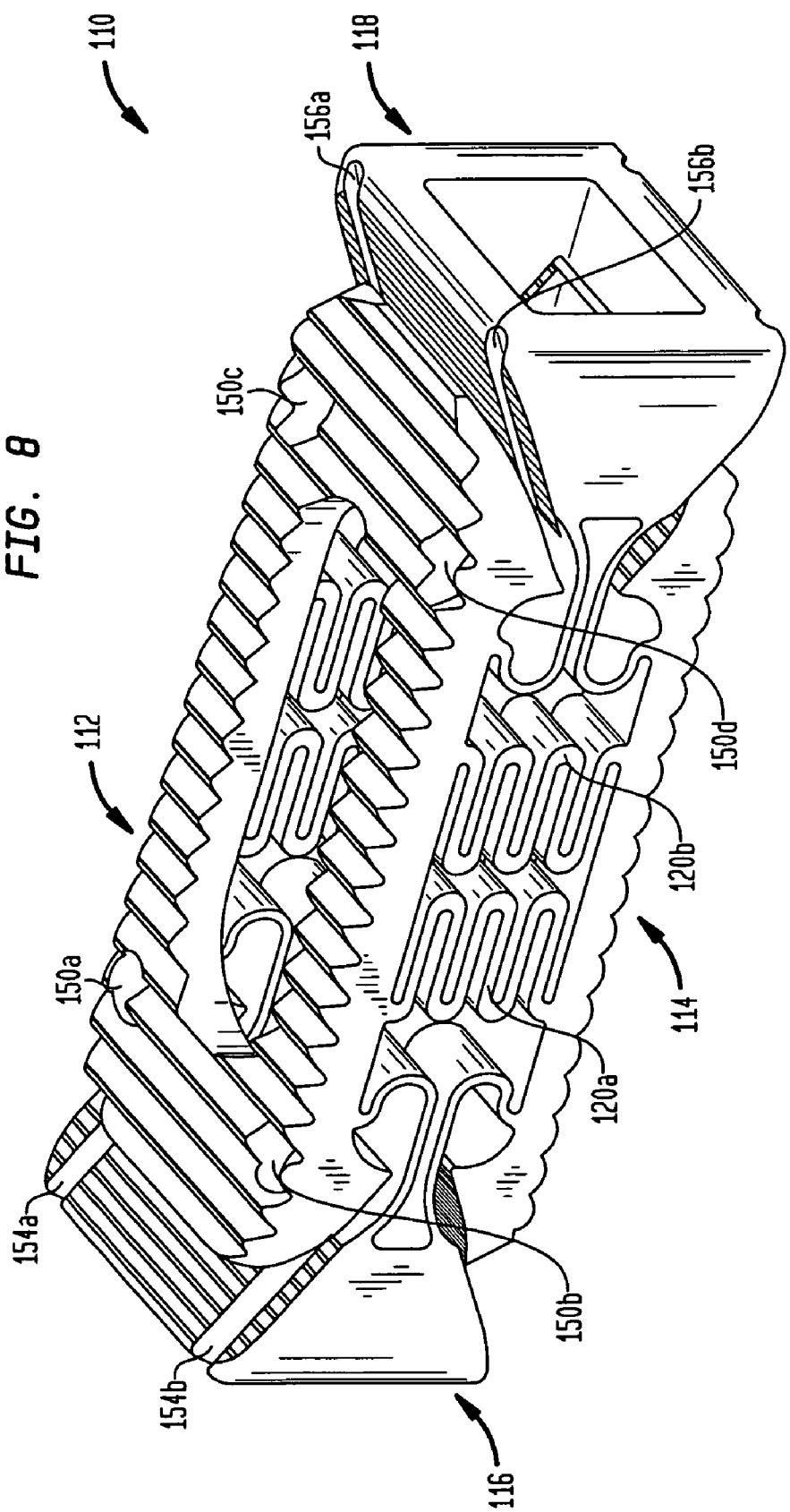
FIG. 8 is another perspective view of the expandable intervertebral implant shown in FIG. 7.
Figure 9:
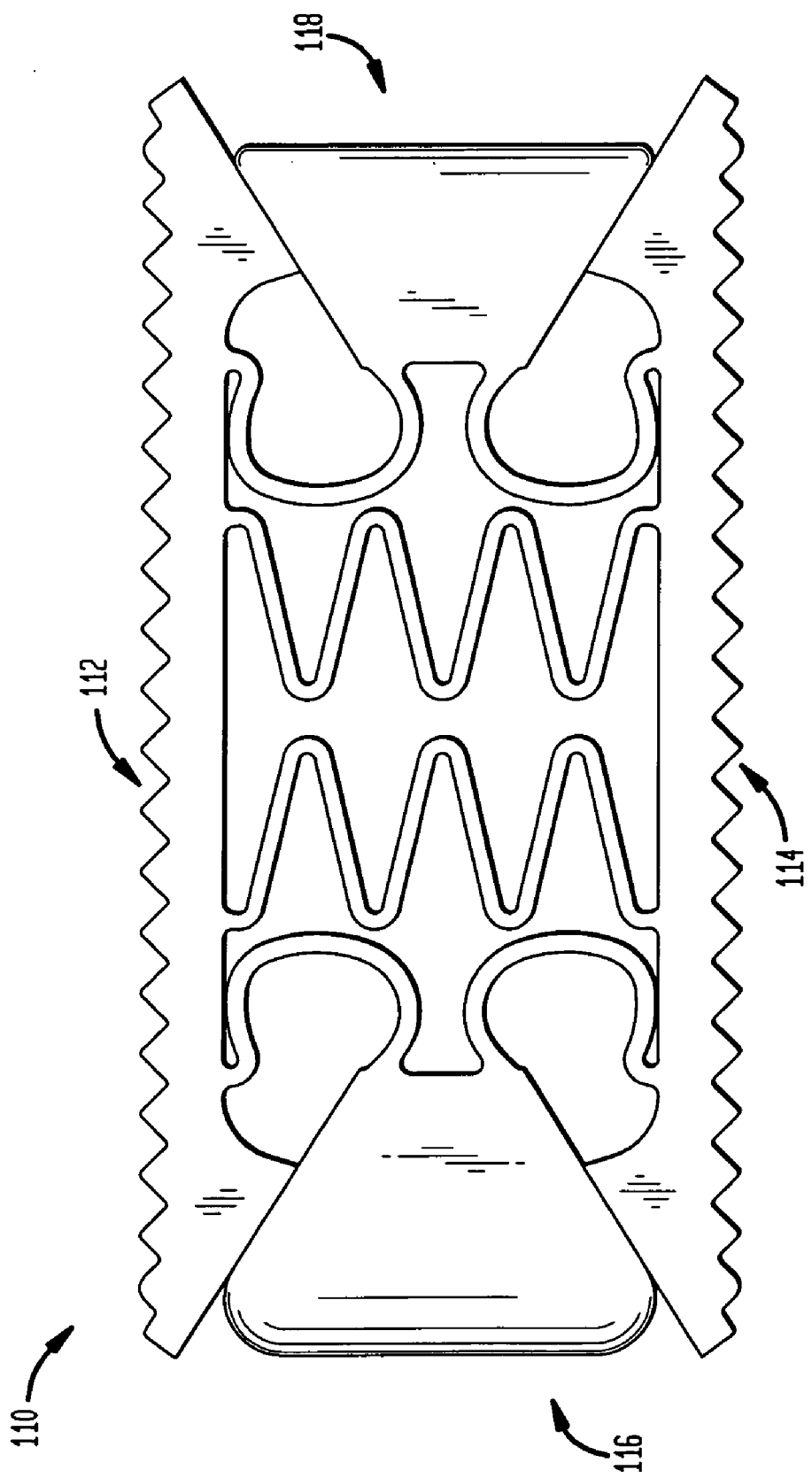
FIG. 9 is a side view of the expandable intervertebral implant shown in FIG. 7 in a fully expanded state.

FIGS. 7-9 depict a second embodiment implant 110. Essentially, implant 110 is substantially similar to implant 10 save for the inclusion of different torsion inhibiting elements. Because of the similarity of implant 110 with implant 10, similar or identical elements will be referred to with like reference numerals within the 100-series of numbers. For example, implant 110 includes first and second members 112 and 114 which are expandable upon movement of first and second wedges 114 and 116 towards one another. However, in the embodiment shown in FIGS. 7-9, first and second members 112 and 114 are provided with apertures (150a-d and 152a-d, respectively) which are capable of receiving protuberances (not shown). For example, these apertures may receive pins, screws, or plugs which extend somewhat below the angled interior surfaces of first and second members 112 and 114, respectively. First and second wedges 116 and 118, on the other hand, each include four channels for cooperation with the protuberances. Specifically, first wedge includes channels 154a-d and second wedge includes channels 156a-d.

The cooperation between the protuberances and channels is like that that similar elements of implant 10 such that movement of wedges 116 and 118 with respect to each other and first and second members 112 and 114 is not inhibited. However, any torsional or rotational movement of the wedges with respect to the first and second members is prevented. In other words, first and second wedges 116 and 118 are prevented from going off track.

Figure 10:
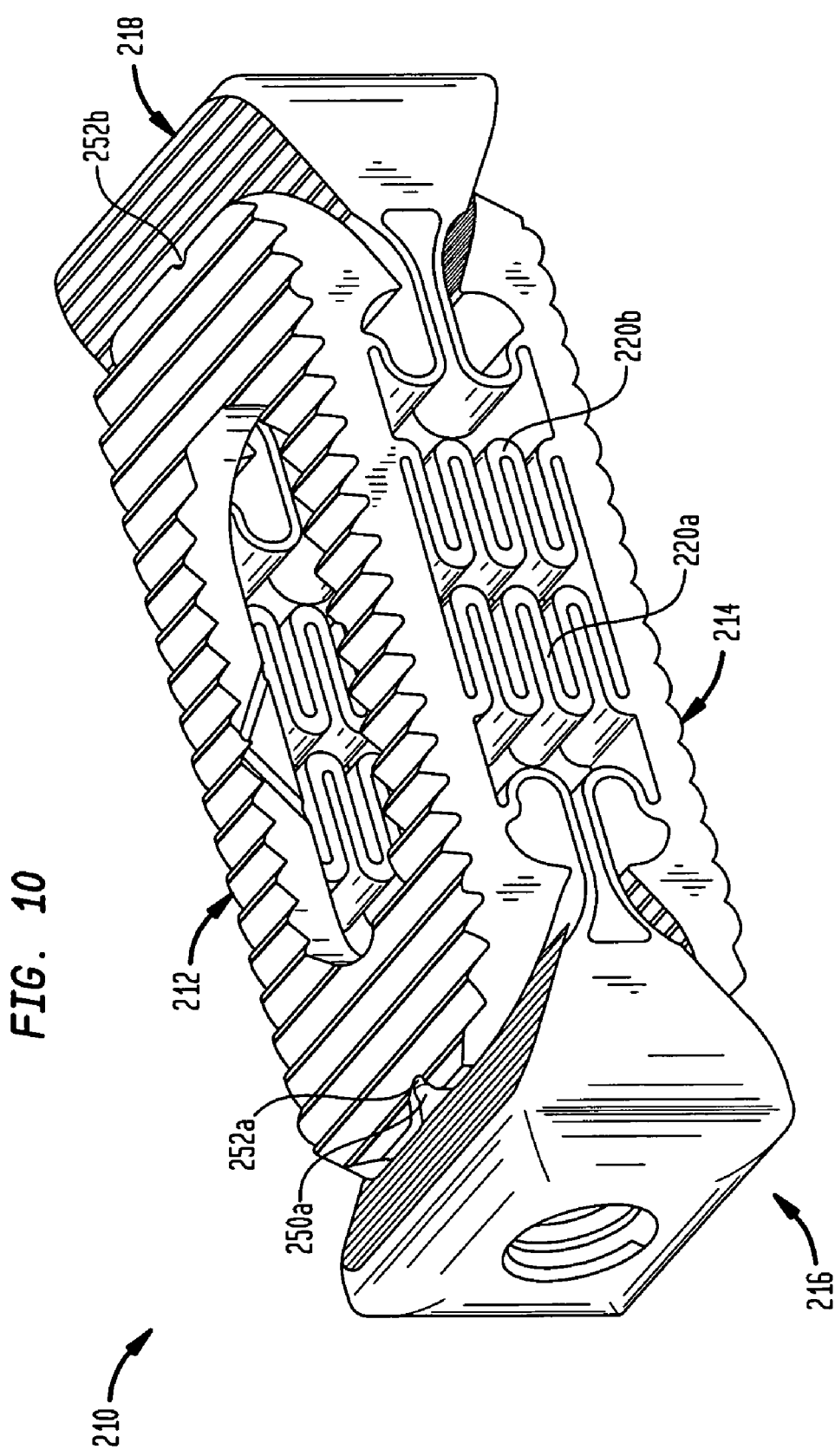
FIG. 10 is a perspective view of an expandable intervertebral implant according to another embodiment of the present invention.
Figure 11:
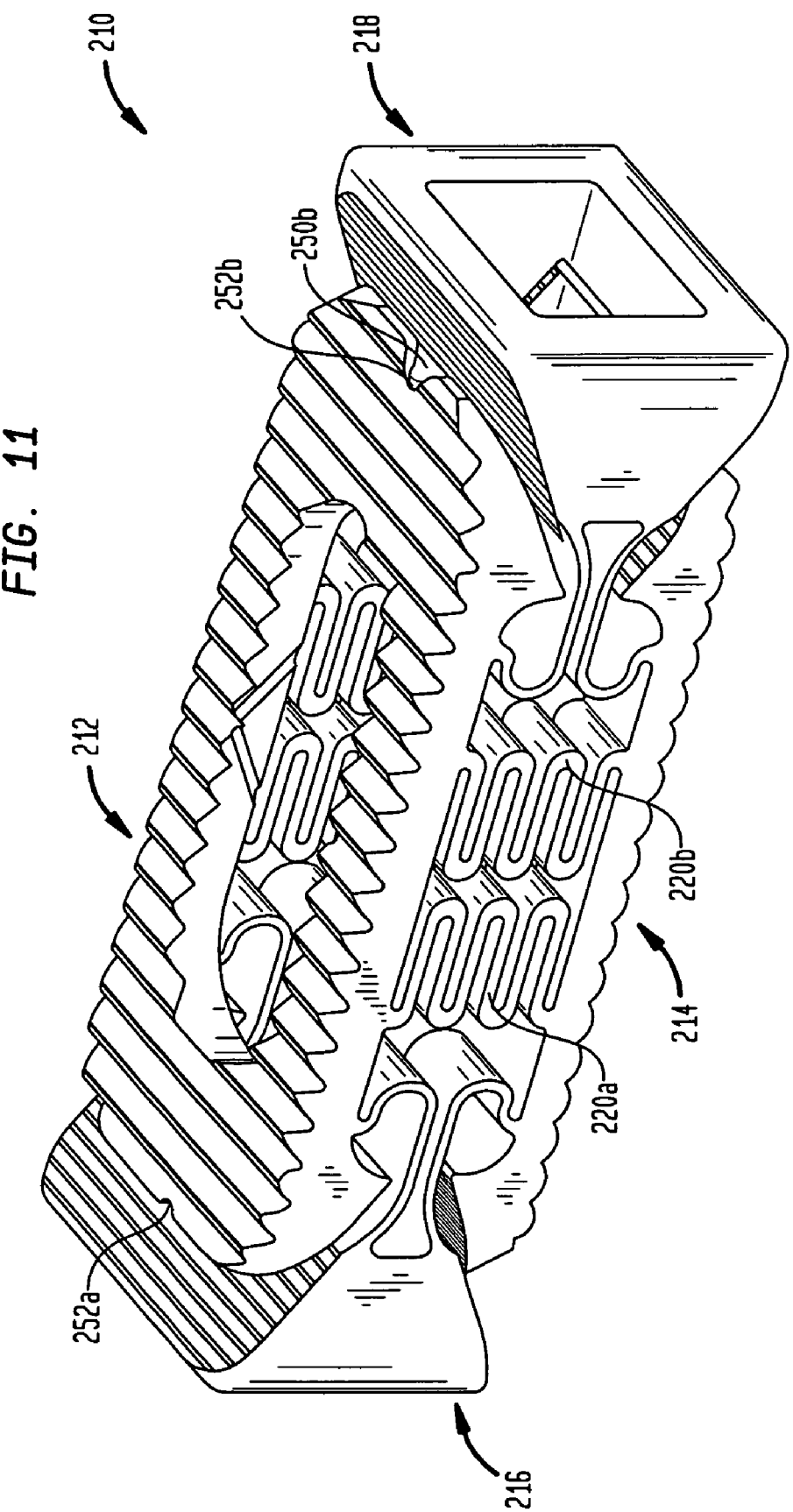
FIG. 11 is another perspective view of the expandable intervertebral implant shown in FIG. 10.
Figure 12:
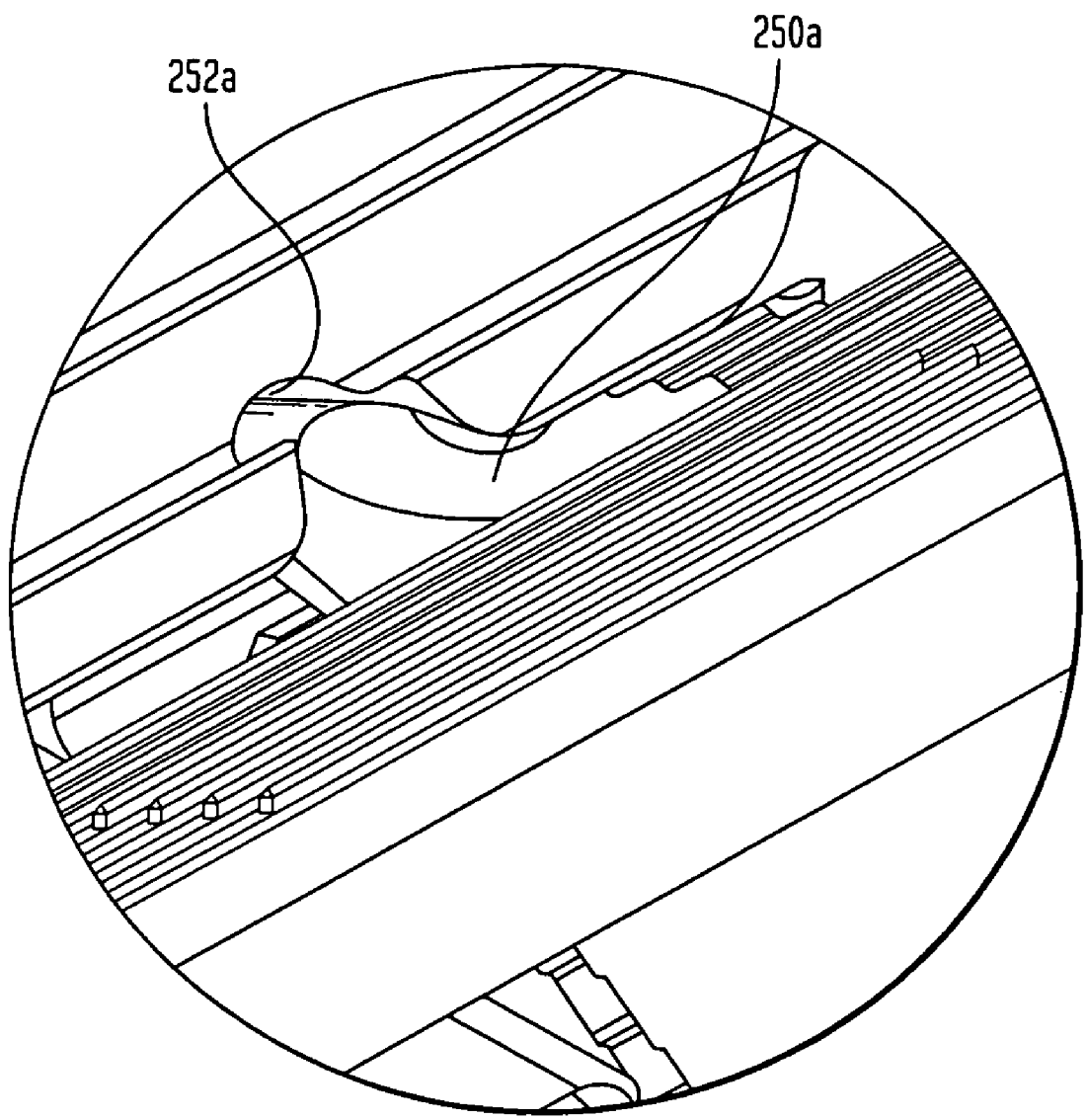
FIG. 12 is an enlarged view of a portion of the expandable intervertebral implant shown in FIG. 10.

FIGS. 10-12 depict yet another embodiment implant 210. Like, implant 110, implant 210 is similar to implant 10, save for the inclusion of different torsion inhibiting elements. Once again, like elements in implant 210 will be referred to within the 200-series of numbers. Instead of including a series of channels and protuberances, the torsion inhibiting elements of implant 210 include a tongue and groove cooperation between its first and second members 212 and 214 and its first and second wedges 216 and 218. Specifically, first wedge 216 is provided with a first tongue 250a for cooperation with a first groove 252a of the first member, and a second tongue 250b for cooperation with a second groove 252b of the first member. Likewise, second wedge 218 is provided with a first tongue 250c for cooperation with a first groove 252c of the first member, and a second tongue 250d for cooperation with a second groove 252d of the second member. These elements cooperate in order to provide a nearly identical function to that of the torsion inhibiting elements discussed above in connection with implant 110. It is to be understood that each of the above discussed torsion inhibiting elements may vary. For instance, the specific shapes of the elements can widely vary. Moreover, the inclusion of certain elements on certain components may be swapped. For example, implant 210 may include wedges employing grooves and first and second members employing tongues.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An impaction instrument comprising:
a rod having a first threaded end, a second end opposite the first threaded end, and a tapered portion disposed between the first and second ends;
a sleeve having an internal channel, and at least two deformable fingers capable of outward expansion upon placement of the rod through the internal channel; and
a locking knob attached to the second end of the rod for fixing the rod and the sleeve with respect to each other.

2. The impaction instrument of claim 1, wherein the tapered portion of the rod is dimensioned to expand the deformable fingers.

3. The impaction instrument of claim 2, wherein the tapered portion has a diameter that increases in a direction from the second end to the first end.

4. The impaction instrument of claim 1, wherein the rod includes a rod shoulder between the first end and the tapered portion.

5. The impaction instrument of claim 4, wherein the sleeve includes a sleeve shoulder.

6. The impaction instrument of claim 1, wherein the locking knob includes a back portion.

7. The impaction instrument of claim 6, wherein the back portion is provided with a coating to accept shock provided by an impaction force.

* * * * *